(12) United States Patent
Yang et al.

(10) Patent No.: US 10,413,564 B2
(45) Date of Patent: Sep. 17, 2019

(54) COMPOSITIONS AND METHODS FOR COMBATING DRUG-RESISTANT CANCERS

(71) Applicant: NATIONAL YANG-MING UNIVERSITY, Taipei (TW)

(72) Inventors: Muh-Hwa Yang, Taipei (TW); Dennis Shin-Shian Hsu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 6 days.

(21) Appl. No.: 15/812,463

(22) Filed: Nov. 14, 2017

(65) Prior Publication Data

US 2018/0280423 A1   Oct. 4, 2018

Related U.S. Application Data

(60) Provisional application No. 62/421,893, filed on Nov. 14, 2016.

(51) Int. Cl.

| | | |
|---|---|---|
| A61K 45/06 | (2006.01) | |
| A61K 38/08 | (2019.01) | |
| A61K 38/10 | (2006.01) | |
| A61K 38/00 | (2006.01) | |
| A61P 35/00 | (2006.01) | |
| C07K 7/06 | (2006.01) | |
| C07K 7/08 | (2006.01) | |
| C07K 7/00 | (2006.01) | |
| A61K 31/7105 | (2006.01) | |
| A61K 39/395 | (2006.01) | |
| A61K 39/00 | (2006.01) | |

(52) U.S. Cl.
CPC .... *A61K 31/7105* (2013.01); *A61K 39/39541* (2013.01); *A61K 45/06* (2013.01); *A61P 35/00* (2018.01); *A61K 2039/505* (2013.01); *A61K 2039/5152* (2013.01)

(58) Field of Classification Search
CPC ...... A61K 2039/505; A61K 2039/5152; A61K 31/7105; A61K 39/39541; A61K 45/06; A61K 38/08; A61K 38/10; A61K 38/00; A61P 35/00; C07K 7/06; C07K 7/08; C07K 7/00
USPC ..... 514/1.1, 19.2, 19.3, 21.5, 21.6; 530/327, 530/328, 300
See application file for complete search history.

(56) References Cited

U.S. PATENT DOCUMENTS 5,661,004 A * 8/1997 Browning ............ C07K 14/525 435/325
2016/0279240 A1* 9/2016 Hung ................. A61K 31/7076

\* cited by examiner

*Primary Examiner* — Julie Ha
(74) *Attorney, Agent, or Firm* — Muncy, Geissler, Olds & Lowe, P.C.

(57) ABSTRACT

Compositions and methods for reducing or overcoming acquired resistance to cetuximab are provided. Compositions and methods for treatment of cetuximab-resistant cancers are also provided. In addition, methods of inhibiting the growth of EGFR-expressing tumor cells that are resistant to cetuximab therapy are provided herein.

18 Claims, 11 Drawing Sheets

Specification includes a Sequence Listing.

COMPOSITIONS AND METHODS FOR COMBATING DRUG-RESISTANT CANCERS

RELATED APPLICATION

This application claims priority to U.S. Provisional Application No. 62/421,893, filed on Nov. 14, 2016, the content of which is hereby incorporated by reference in its entirety.

TECHNICAL FIELD OF THE INVENTION

The invention relates to the field of cancer therapy. Specifically, the invention relates to compositions and methods for reducing and overcoming acquired resistance to cetuximab. The invention also relates to compositions and methods for treatment of cetuximab-resistant cancers. Additionally, the invention relates to methods for treating cetuximab-resistant cancers using a combination of an EGFR antagonist and an NF-κB antagonist.

BACKGROUND OF THE INVENTION

Cancer is a serious health issue all around the world. Despite recent advancements made in treating cancers, it is often observed that with exceptions, a cancer treatment fails to cure a patient. One of the main causes of failure in the treatment of cancer is the development of drug resistance by the cancer cells. For example, after several cycles of therapy, some tumor cells become resistant to the therapeutic agent, which results in a loss of response to further therapy.

Head and neck squamous cell carcinoma (HNSCC), which comprises the cancers originating from the oral cavity, oropharynx, larynx, and hypopharynx, is one of the major cancers worldwide. In recent years, targeting epidermal growth factor receptor (EGFR) has become a major strategy for combating late-stage HNSCC because EGFR overexpression is observed in approximately 90% of HNSCC cases and is associated with an unfavorable outcome (Grandis J. R. et al., *Cancer Res* 53:3579-84 (1993), Chung C. H. et al., *J Clin Oncol* 24: 4170-6 (2006)).

Pivotal clinical studies demonstrated that cetuximab, a humanized IgG1 monoclonal antibody against the extracellular domain of EGFR, is effective in advanced HNSCC patients when combined with radiation or chemotherapy (Vormorken J. B. et al., *N Engl J Med* 359:1116-27 (2008)). Therefore, cetuximab has been regarded as a major treatment for advanced or recurrent/metastatic HNSCC. However, the improvement in survival afforded by cetuximab is not as extensive as expected (Bonner J. A. et al., *Lancet Oncol* 11:21-8 (2010)). Notably, although the initial response rate to cetuximab in HNSCC is high, most of the patients eventually develop resistance to cetuximab, i.e., acquired resistance (Rabinowits G. et al., *Oral Oncol* 48:1085-9 (2012)), and the efficacy of cetuximab as second-line therapy after chemotherapy failure is far behind its performance in first-line treatment.

Overcoming acquired resistance to cetuximab is of utmost importance for cancer, such as advanced HNSCC.

SUMMARY OF THE INVENTION

The present disclosure is based, at least in part, on the unexpected discovery that acquired resistance to cetuximab undergo a Snail-induced epithelial-mesenchymal transition (EMT), and LTβ is crucial for Snail-induced cetuximab resistance. Elevated expression level of LTβ is observed in cetuximab-resistant cells Inhibition of LTβ combats the acquired resistance to cetuximab, and some peptides comprising appear to be effective in overcoming resistance to cetuximab in cancer cells. Use of an LTβ antagonist (e.g. an LTβ neutralizing antibody or an antisense nucleic acid) or such a peptide is capable of combating acquired resistance to cetuximab. Combination use of an LTβ antagonist or such a peptide with an anti-EGFR antibody is useful for treating cetuximab-resistant cancers.

The present disclosure is also based on the finding that the combination of an EGFR antagonist with an NF-κB antagonist successfully overcomes cetuximab resistance in cancer cells, as demonstrated by (1) an enhanced inhibitory effect in cetuximab-resistant HNSCC cells, and (2) a significant synergistic effect in zebrafish model. The composition comprising an EGFR antagonist and an NF-κB antagonist restored sensitivity to cetuximab in the cetuximab-resistant model.

Accordingly, one aspect of the present disclosure relates to a method for treating cancer, in particular, cetuximab-resistant cancer in a subject, comprising administering to a subject in need thereof an EGFR antagonist in combination with an NF-κB antagonist in an amount effective in treating cancer. The EGFR antagonist and the NF-κB antagonist may be co-administered simultaneously, separately, or sequentially. In some embodiments, the subject has an elevated expression level of LTβ.

In some embodiments, the EGFR antagonist used in the methods described herein is an antibody against EGFR, such as cetuximab, panitumumab or nimotuzumab. Alternatively, the EGFR antagonist used in the methods described herein is a small-molecule EGFR tyrosine kinase inhibitor, such as afatinib, erlotinib, gefitinib, lapatinib, icotinib, neratinib or vandetanib.

In some embodiments, the NF-κB antagonist used in the methods described herein is a small-molecule inhibitor that suppresses NF-κB signaling pathway. Such a small-molecule inhibitor can be a proteasome inhibitor, such as parthenolide or bortezomib.

In some embodiments, the EGFR antagonist described herein is selected from a group consisting of afatinib, erlotinib, gefitinib and lapatinib, and the NF-κB antagonist described herein is parthenolide or bortezomib. In one example, the EGFR antagonist is afatinib, and the NF-κB antagonist is bortezomib.

Another aspect of the present disclosure relates to a method of reducing or overcoming acquired resistance to cetuximab in a patient. The method described herein comprises administering to a patient a composition comprising an agent that is an antagonist of Lymphotoxin-β (LTβ), in which the antagonist is an LTβ neutralizing antibody or an antisense nucleic acid such as a small hairpin RNA (shRNA), a small interfering RNA (siRNA) or a micro RNA (miRNA). In some embodiments, the patient has an elevated expression level of LTβ.

In some embodiments, the antibody is an LTβ neutralizing antibody. In some embodiments, the antibody is a polyclonal antibody. In some embodiments, the antibody is a monoclonal antibody. The antibody described herein is capable of neutralizing an LTβ (i.e., binding to the LTβ and blocking the signal transduction mediated by LTβ) and can be a naturally-occurring antibody (e.g., a monoclonal antibody), an antigen-binding fragment thereof, or a genetically engineered antibody (e.g., human antibody, a humanized antibody, a chimeric antibody, a mouse antibody or a single-chain antibody) that neutralizes LTβ, i.e., binding to either antigen and blocking the signaling pathway mediated by it.

In some embodiments, the antisense nucleic acid is a short hairpin RNA (shRNA). In certain embodiments, the shRNA comprises a sense strand having the nucleotide sequence of CCGGCGAGAGGGTGTACGTCAACATCTCGAGATGT-TGACGTACACCCTCTCGTTTTT G (SEQ ID NO: 11) and an antisense strand that hybridizes under stringent conditions to the sense strand. The shRNA described herein is capable of inhibiting expression of LTβ gene.

In some embodiments, the composition further comprises a cytotoxic, chemotherapeutic, or anti-cancer agent for treating tumors.

The patient to be treated in the method described herein may have a tumor that has acquired resistance to cetuximab. The patient may be characterized by the absence of PIK3CA gene mutation, the absence of EGFR gene mutation, and/or the presence of wild-type RAS family genes (e.g. KRAS, HRAS, NRAS). In some embodiments, the patient is characterized by the absence of PIK3CA, KRAS, HRAS, NRAS, and EGFR gene mutation. In some embodiments, ERBB2 gene is not amplified in the tumor cells.

The method described herein may further comprise anti-EGFR antibody for treating cancer. The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

Another aspect of the present disclosure relates to a composition comprising a peptide comprising an amino acid sequence of QDGLYYLYCLVGYR (SEQ ID NO: 5) or ERVYVNISH (SEQ ID NO: 9) or a combination thereof.

Another aspect of the present disclosure relates to a method of reducing or overcoming acquired resistance to cetuximab in a patient. The method described herein comprises administering to a patient a composition comprising a peptide that comprises an amino acid sequence of QDGLYYLYCLVGYR (SEQ ID NO: 5) or ERVYVNISH (SEQ ID NO: 9) or a combination thereof. In some embodiments, the patient has an elevated expression level of LTβ.

In some embodiments, the peptide described herein comprises an amino acid sequence of QDGLYYLYCLVGYR (SEQ ID NO: 5). In some embodiments, the peptide described herein comprises an amino acid sequence of ERVYVNISH (SEQ ID NO: 9).

The patient to be treated in the method described herein may have a tumor that has acquired resistance to cetuximab. The patient may be characterized by the absence of PIK3CA gene mutation, the absence of EGFR gene mutation, and/or the presence of wild-type RAS family genes (e.g. KRAS, HRAS, NRAS). In some embodiments, the patient is characterized by the absence of PIK3CA, KRAS, HRAS, NRAS, and EGFR gene mutation. In some embodiments, ERBB2 gene is not amplified in the tumor cells.

The method described herein may further comprise anti-EGFR antibody for treating cancer. The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

In some embodiments, the treatment method described herein further comprises administering at least one cytotoxic, chemotherapeutic, or anti-cancer agent to the patient.

Another aspect of the present disclosure relates to a pharmaceutical composition that comprises a combination of an anti-EGFR antibody and a peptide described herein, and a pharmaceutically effective carrier.

In some embodiments, the peptide described herein comprises an amino acid sequence of QDGLYYLYCLVGYR (SEQ ID NO: 5). In some embodiments, the peptide described herein comprises an amino acid sequence of ERVYVNISH (SEQ ID NO: 9).

The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

Another aspect of the present disclosure relates to a method for treating cancer wherein the cancer is resistant to cetuximab, the method comprising administering a therapeutically effective amount of a pharmaceutical composition that comprises a combination of an anti-EGFR antibody and a peptide described herein to a patient suffering therefrom. In some embodiments, the patient has an elevated expression level of LTβ.

In some embodiments, the method described herein further comprises administering at least one cytotoxic, chemotherapeutic, or anti-cancer agent to the patient.

The patient to be treated in the method described herein may have a tumor that has acquired resistance to cetuximab. The patient may be characterized by the absence of PIK3CA gene mutation, the absence of EGFR gene mutation, and/or the presence of wild-type RAS family genes (e.g. KRAS, HRAS, NRAS). In some embodiments, the patient is characterized by the absence of PIK3CA, KRAS, HRAS, NRAS, and EGFR gene mutation. In some embodiments, ERBB2 gene is not amplified in the tumor cells.

Another aspect of the present disclosure relates to a method of inhibiting the growth of EGFR-expressing tumor cells that are resistant to cetuximab treatment, the method comprising contacting the tumor cells with an effective amount of a combination of anti-EGFR antibody and a peptide, wherein the peptide comprises an amino acid sequence of QDGLYYLYCLVGYR (SEQ ID NO: 5) or ERVYVNISH (SEQ ID NO: 9) or a combination thereof. In some embodiments, the cells have an elevated expression level of LTβ.

Another aspect of the present disclosure relates to a method of inhibiting the growth of EGFR-expressing tumor cells that are resistant to cetuximab treatment, the method comprising contacting the tumor cells with an EGFR antagonist in combination with an NF-κB antagonist in an amount effective in treating cancer. In some embodiments, the cells have an elevated expression level of LTβ.

Within the scope of this disclosure, cancer described herein includes, but is not limited to, head and neck cancer, head and neck squamous cell carcinoma (HNSCC), colorectal cancer, breast cancer, lung cancer, kidney cancer, thyroid cancer, brain cancer (glioma), ovarian cancer, pancreatic cancer, prostate cancer, plasma cell cancer (myeloma), liver cancer, muscle cancer (sarcoma), neuroblastoma, lymphoma, stomach cancer, adenoid cystic carcinoma, skin cancer including melanoma, basal cell carcinoma, or squamous cell carcinoma. In some embodiments, the cancer is a head and neck cancer, head and neck squamous cell carcinoma (HNSCC) or colorectal cancer. In some examples, the cancer can be a locally or regionally advanced HNSCC. Alternatively, the cancer can be a recurrent or metastatic HNSCC. In some embodiments, the cancer is a colorectal cancer. In one example, the cancer is a metastatic colorectal cancer.

Also within the scope of this disclosure are (a) pharmaceutical compositions for use in reducing or overcoming cetuximab-resistant cancer in a subject, the pharmaceutical composition comprising an antagonist of LTβ or a peptide described herein; and (b) uses of the just-described pharmaceutical composition in manufacturing a medicament for treating cetuximab-resistant cancer.

In addition, within the scope of this disclosure are (a) pharmaceutical compositions for use in treating cancer or drug-resistant cancer (e.g., cetuximab-resistant cancer) in a subject, the pharmaceutical composition comprising an EGFR antagonist and an NF-κB antagonist described herein; and (b) uses of the just-described pharmaceutical composition in manufacturing a medicament for treating cancer or drug-resistant cancer such as cetuximab-resistant cancer.

The present disclosure also provides kits comprising a pharmaceutical composition described herein. The kits may include a single dose or multiple doses of the provided pharmaceutical composition. The provided kits may be useful for overcoming cetuximab-resistant cancer. The provided kits may be useful for treating cetuximab-resistant cancer. In certain embodiments, the kits described herein further include instructions for administering the provided pharmaceutical composition or packaging information. The kit may also optionally include a device for administration of the pharmaceutical composition (e.g. a syringe for parenteral administration).

The details of one or more embodiments of the disclosure are set forth in the description below. Other features or advantages of the present disclosure will be apparent from the following drawings and detailed description of several embodiments, and also from the appended claims.

The β-sheets of LTβ are indicated. P5 (SEQ ID NO: 5), P8 (SEQ ID NO: 8) and P9 (SEQ ID NO: 9) interact with EGFR-ECD.

Figure 6:
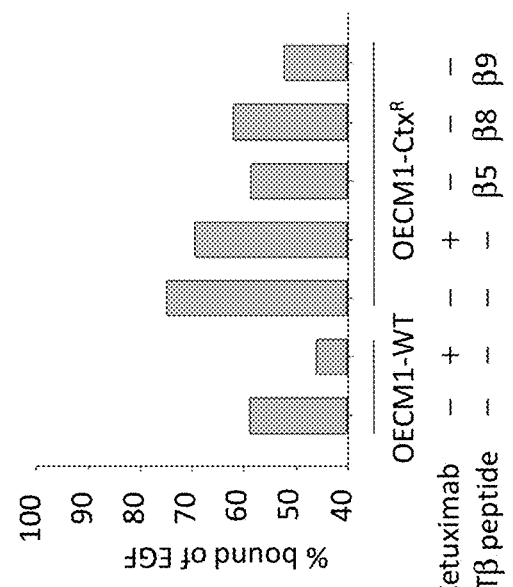

FIG. 6 shows the EGF binding of parental OECM1 and OECM1-Ctx$^R$ cells treated with/without cetuximab and peptides of LTβ β-sheets.

Figure 7:
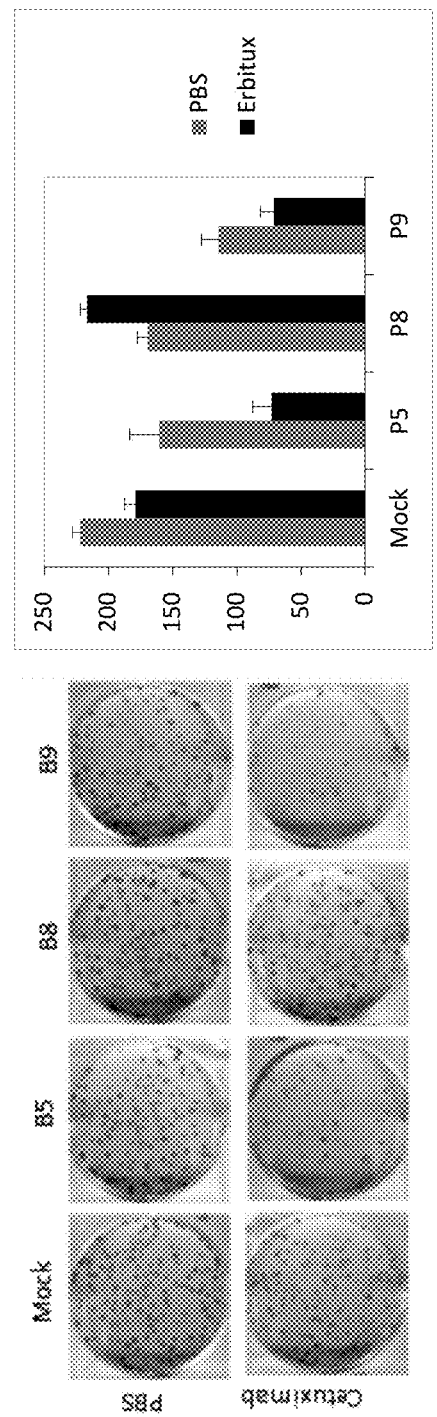

FIG. 7 shows the clonogenecity assay. The OECM1-Ctx$^R$ cells were treated with peptides of different LTβ β-sheets in the absence/presence of cetuximab (Erbitux), then were plated onto dishes for 10 days. The colonies were stained with crystal violet and counted if the size was great than 0.5 mm.

Figure 8:
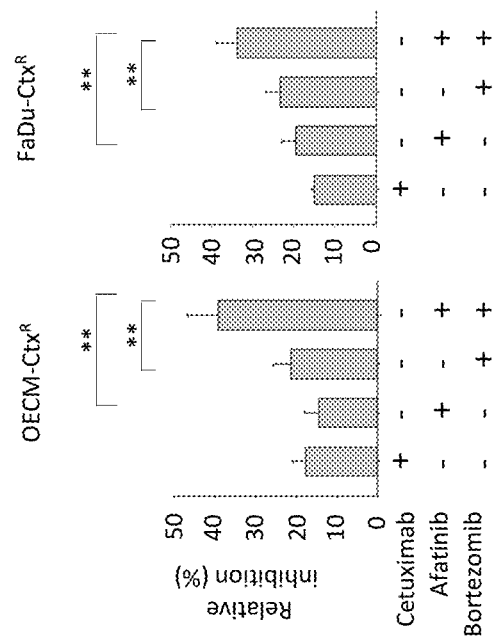

FIG. 8 shows the relative growth inhibition by cetuximab of OECM1-Ctx$^R$ cells (left) and FaDu-Ctx$^R$ cells (right) treated with cetuximab, afatinib, bortezomib, or both afatinib and bortezomib. Data represent mean±S.D. n=3. **p<0.01 (Student's t test).

Figure 9:
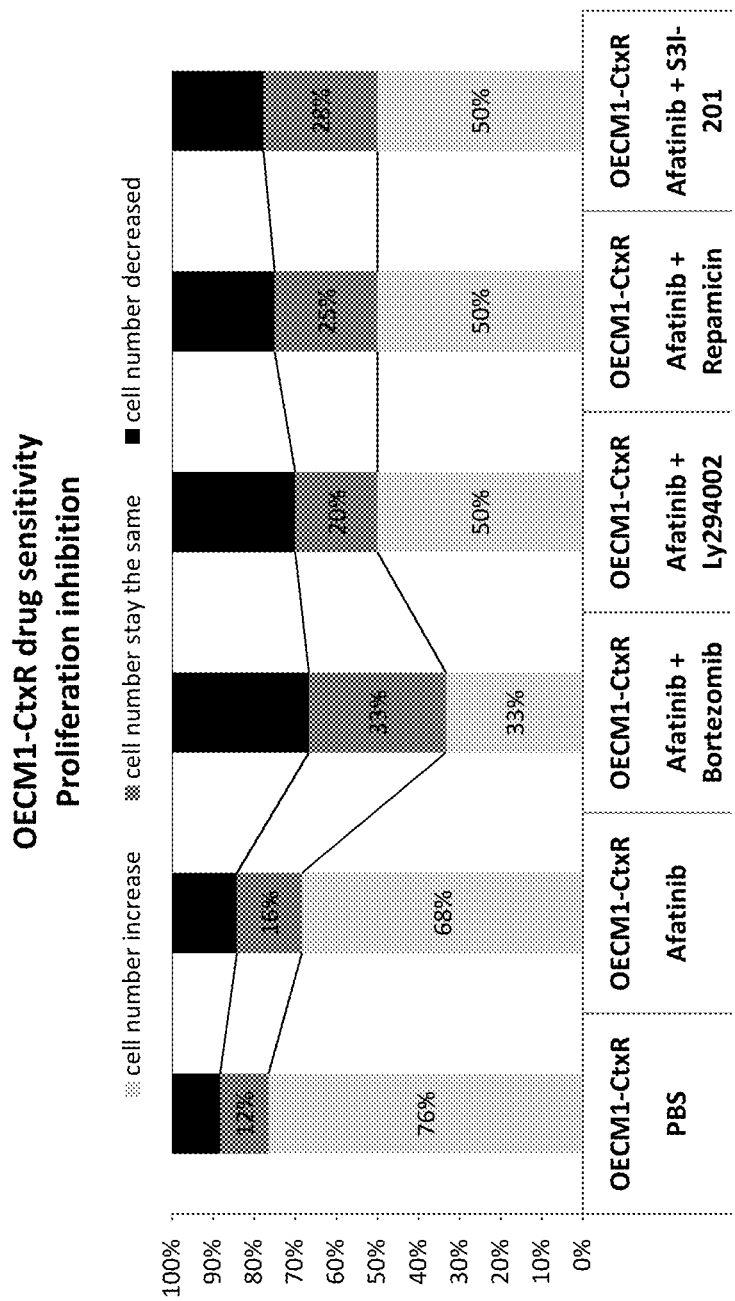

FIG. 9 shows the quantification of OECM1-Ctx$^R$ engrafted and proliferated in the zebrafish xenotransplantation model without drug (PBS) or with various combination of drugs.

Figure 10:
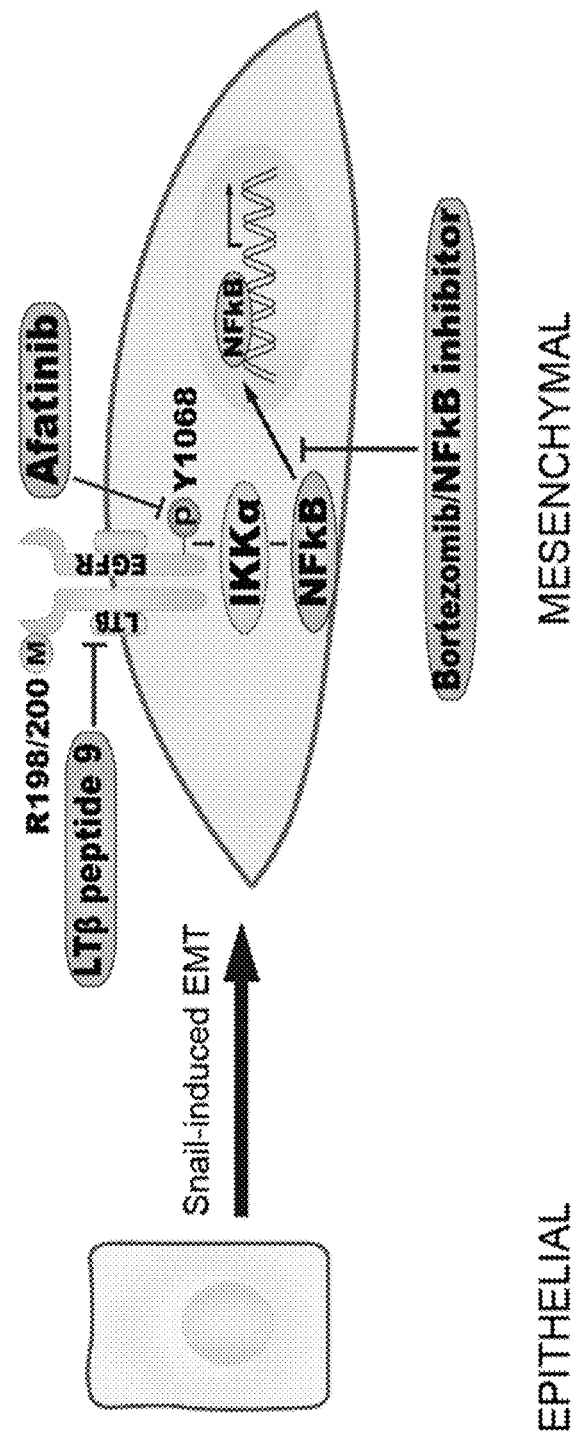

FIG. 10 shows a schema for the mechanism of acquired resistance to cetuximab in head and neck cancer cells. When the cancer cells undergo Snail-induced EMT, the methylated EGFR interacts with LTβ, resulting in EGFR activation. Activated EGFR promotes NF-κB activation through IKKα to engender cetuximab resistance. Inhibition of EGFR phosphorylation by afatinib, NF-κB activation by bortezomib or other NF-κB inhibitors, and interception of the interaction beween LTβ and methylated EGFR by the peptide of 9$^{th}$ β-strand of LTβ reverse the cetuximab resistance.

Figure 11:
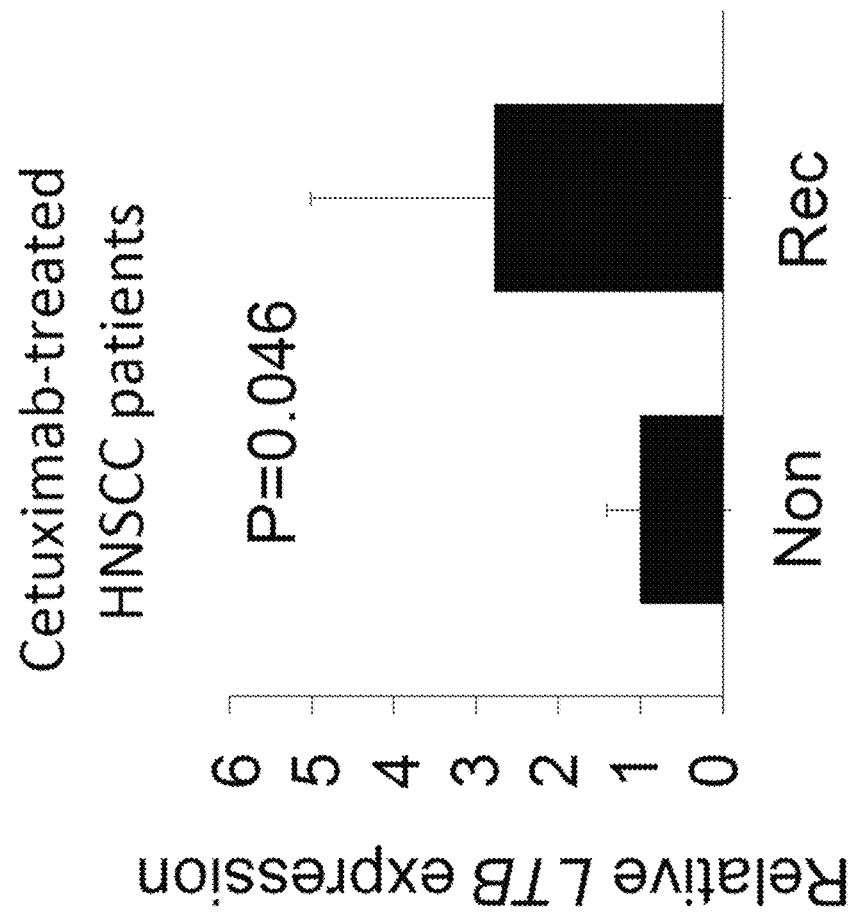

FIG. 11 shows the result of relative expression of LTB in 12 cetuximab-treated patients with HNSCC (4 with and 8 without recurrence). The result is presented as the fold change of LTB expression in tumors with related to the corresponding normal counterparts. For calculating the result, the data from both tumor and normal tissues were normalized with the internal control GAPDH first and then the tumor-to-normal fold changes of LTB were obtained. Non, non-recurrence (n=8); Rec, recurrence (n=4). Data represent mean±SD. P value is estimated by the Student t test.

DETAILED DESCRIPTION OF THE INVENTION

Cetuximab is a recombinant human and mouse chimeric monoclonal IgG1 antibody that binds to and inhibits the biologic activity of the human epidermal growth factor receptor (EGFR). Cetuximab is distributed under the trade name Erbitux in the U.S. and Canada by the drug company Bristol-Myers Squibb and outside the U.S. and Canada by the drug company Merck KGaA. In Japan, Merck KGaA, Bristol-Myers Squibb and Eli Lilly have a co-distribution.

Cetuximab is used for the treatment of metastatic colorectal cancer, metastatic non-small cell lung cancer and head and neck cancer. Cetuximab was approved by the FDA in 2006 for use in combination with radiation therapy for treating squamous cell carcinoma of the head and neck (SCCHN) or as a single agent in patients who have had prior platinum-based therapy. In 2009, the FDA approved cetuximab for treatment of colon cancer with wild-type KRAS, since it had little or no effect in colorectal tumors harboring a KRAS mutation (this also applied to the EGFR antibody panitumumab).

Cetuximab is a major treatment for advanced head and neck squamous cell carcinoma (HNSCC). In HNSCC, the incidence of RAS mutation, which is the major cause of cetuximab resistance, is relatively rare compared with the other types of cancers. However, the improvement in survival after cetuximab treatment is not as extensive as expected, and most patients eventually develop acquired resistance despite their initial responses. The Applicant elucidates the mechanism of driver gene mutations-independent mechanism of acquired resistance to cetuximab in HNSCC, and discovered strategies for combating cetuximab resistance.

Combination Therapy for Cancer or Cetuximab-Resistant Cancer Treatment

The present disclosure is based on the discovery that Snail is crucial in the development of acquired resistance to cetuximab in HNSCC, which is independent from the known driver genes mutations. LTβ is the key molecule in mediating Snail-induced cetuximab resistance in HNSCC. LTβ interacts with EGFR to enhance EGFR-ligand binding and to promote EGFR phosphorylation. Importantly, LTβ activates NF-κB signal pathways and increases EGFR phosphorylation in cetuximab-resistant head and neck cancer cells. Cetuximab resistant cancers can be overcome by the combination of EGFR inhibiting agent (e.g. afatinib) and NF-κB inhibiting agent (e.g. bortezomib) that provides a higher inhibitory effect for cetuximab resistant cancer such as HNSCC. A synergistic effect of EGFR inhibiting agent (e.g. afatinib) and NF-kB inhibiting agent (e.g. bortezomib) was demonstrated in vitro and in vivo using the zebrafish model.

Accordingly, the present disclosure relates to a method for treating cancer or drug-resistant cancer such as cetuximab-resistant cancer in a subject, comprising administering to a subject in need thereof an EGFR antagonist in combination with an NF-κB antagonist in an amount effective in treating cancer. In preferred embodiments, the method described herein is used for treating cetuximab-resistant cancer.

In a combination therapy regimen, the compositions used in the methods of the present disclosure are administered in a therapeutically effective or synergistic amount. As used herein, a therapeutically effective amount is such that co-administration of an EGFR antagonist and an NF-κB antagonist results in reduction or inhibition of cancer or drug-resistant cancer. A therapeutically synergistic amount is that amount of an EGFR antagonist and an NF-κB antagonist necessary to synergistically or significantly reduce or eliminate cancer or drug-resistant cancer. The compositions used in the methods may be co-administered simultaneously, separately, or sequentially in the treatment of a patient, such as a cancer patient.

The subject to be treated in any of the method described herein may be a human patient suffering from cancer, in particular, cancer resistant to cetuximab. In some embodiments, the subject is a human cancer patient who is resistant to cetuximab therapy. In some embodiments, the subject to be treated by the method described herein may be characterized by increased Snail expression. In some embodiments, the subject may be characterized by increased LTβ expression. In some embodiments, the subject may be characterized by EGFR expression or overexpression with or without EGFR gene mutation (e.g. in exons 19-21). In some embodiments, the subject may be characterized by no mutation in EGFR. In some embodiments, the subject may be characterized by no mutation in PIK3CA. In some embodiments, the subject may be characterized by no mutation in RAS family genes (e.g. KRAS, HRAS, NRAS). In some embodiments, the subject may be characterized by wild-type RAS family genes (e.g. KRAS, HRAS, NRAS). In some embodiments, the subject may be characterized by no ERBB2 amplification.

In some embodiments, the methods described herein may further comprise administering at least one cytotoxic, chemotherapeutic, or anti-cancer agent to the patient.

Methods of Reducing/Overcoming Acquired Resistance to Cetuximab

The present disclosure is based on the finding that acquired resistance to cetuximab undergo a Snail-induced epithelial-mesenchymal transition (EMT), and LTβ is crucial for Snail-induced cetuximab resistance. Lymphotoxin-β (LTβ) is a TNF family membrane protein and plays major a role in the lymphoid cells. Lymphotoxin-beta (LTβ) also known as tumor necrosis factor C (TNF-C) is a protein that in humans is encoded by the LTB gene. The Applicants found expression level of LTβ was increased in cetuximab-resistant cancer cells. Higher expression level of LTB was also found in samples obtained from patients who developed cetuximab resistance after treatment. Knockdown of LTβ increased cetuximab sensitivity in cetuximab-resistant cancer cells, and sensitized the primary HNSCC cells obtained from a cetuximab resistance patient. Use of an antagonist of Lymphotoxin-β (LTβ) such as an LTβ neutralizing antibody or an antisense nucleic acid, can combat the resistance to cetuximab in cancer cells.

Accordingly, one aspect of the present disclosure relates to a method of reducing or overcoming acquired resistance to cetuximab using a composition comprising an agent that is an antagonist of Lymphotoxin-β (LTβ), in which the antagonist is an LTβ neutralizing antibody or an antisense nucleic acid such as a small hairpin RNA (shRNA), a small interfering RNA (siRNA) or a micro RNA (miRNA).

The patient to be treated in any of the method described herein is a human patient suffering from cancer, in particular, cancer resistant to cetuximab. In some embodiments, the subject is a human cancer patient who is resistant to cetuximab therapy.

The patient to be treated in the method described herein may be characterized by the elevated expression level of LTβ, the absence of EGFR gene mutation, the absence of EGFR gene mutation, the absence of ERBB2 gene amplification, and/or the presence of wild-type RAS family genes.

In some embodiments, the patient to be treated by the method described herein may be characterized by increased Snail expression. In some embodiments, the patient may be characterized by increased LTβ expression. In some embodiments, the patient may be characterized by EGFR expression or overexpression with or without EGFR gene mutation (e.g. in exons 19-21). In some embodiments, the patient may be characterized by no mutation in EGFR. In some embodiments, the patient may be characterized by no mutation in PIK3CA. In some embodiments, the patient may be characterized by no mutation in RAS family genes. In some embodiments, the patient may be characterized by wild-type RAS family genes. In some embodiments, the patient may be characterized by no ERBB2 amplification.

In some embodiments, the patient to be treated in the method described herein may have a tumor that has acquired resistance to cetuximab. The patient may be characterized by the absence of PIK3CA gene mutation, the absence of EGFR gene mutation, and/or the presence of wild-type RAS family genes (e.g. KRAS, HRAS, NRAS). In some embodiments, the patient is characterized by the absence of PIK3CA, KRAS, HRAS, NRAS, and EGFR gene mutation. In some embodiments, ERBB2 gene is not amplified in the tumor cells.

The method described herein may further comprise anti-EGFR antibody for treating cancer. The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

Anti-LTβ Antibodies

The LTβ neutralizing antibody (anti-LTβ antibody) used in the methods described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made. The anti-LTβ antibody described herein is capable of neutralizing an LTβ (i.e., binding to the LTβ and blocking the signal transduction mediated by LTβ) and can be a naturally-occurring antibody (e.g., a monoclonal antibody), an antigen-binding fragment thereof, or a genetically engineered antibody (e.g., human antibody, a humanized antibody, a chimeric antibody, a mouse antibody or a single-chain antibody) that neutralizes LTβ, i.e., binding to either antigen and blocking the signaling pathway mediated by it.

As used herein, the term "antibody" encompasses not only intact (e.g., full-length) polyclonal or monoclonal antibodies, but also antigen-binding fragments thereof (such as Fab, Fab', F(ab')$_2$ and Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins may be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma and mu, respectively. The subunit structures and three-dimensional configurations of different classes of immunoglobulins are well known.

Antisense Nucleic Acids

An antisense nucleic acid of LTβ, DNA or RNA, is an oligonucleotide capable of forming base-pairs with the LTβ gene (either the sense chain or the antisense chain), thereby suppressing its expression. Preferably, the oligonucleotide has a maximum length of 150 (e.g., 100, 80, 60, or 40) nucleotides.

The antisense nucleic acid can be a double-strand RNA (dsRNA) that inhibits the expression of LTβ via RNA interference. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (shRNA chain forming a tight hairpin structure), both of which can be designed based on the sequence of the target gene. Alternatively, it can be a microRNA.

Preferably, an antisense nucleic acid as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the antisense nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166, 315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

In another example, the antisense nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Hely. Chim. Acta, 1995, 78, 486-504.

In yet another example, the antisense nucleic acid includes one or more modified native nucleobases (i.e., adenine, guanine, thymine, cytosine and uracil). Modified nucleobases include those described in U.S. Pat. No. 3,687, 808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and 0-6 substituted purines (e.g., 2-aminopropyladenine, 5-propynyluracil and 5-propynylcytosine). See Sanghvi, et al., eds., Antisense Research and Applications, CRC Press, Boca Raton, 1993, pp. 276-278).

Any of the antisense nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

The short hairpin RNA (hereafter referred to as "shRNA") capable of inhibiting expression of LTβ of the present invention exhibits LTβ-specific RNAi action when it targets an mRNA portion of thymidylate synthase. Accordingly, the short hairpin RNA can remarkably inhibit LTβ expression. Here, when the RNAi molecule of the present invention "targets an mRNA portion," this means that the antisense strand of shRNA described in detail below can hybridize to a target mRNA portion under stringent conditions.

Stringent conditions can be determined based on the melting temperature (Tm) for nucleic acid at which a hybrid is formed in accordance with a conventional method. For instance, washing conditions that allows maintenance of hybridization comprise, for example, generally "1×SSC, 0.1% SDS, 37° C.," more strictly "0.5×SSC, 0.1% SDS, 42° C.," and further strictly "0.1×SSC, 0.1% SDS, 65° C."

The shRNA of the present invention comprises a sense strand having a nucleotide sequence of ORF encoding TS or a nucleotide sequence partially identical thereto and an antisense strand that hybridizes under stringent conditions to the sense strand. Here, the phrase "a nucleotide sequence of ORF or a nucleotide sequence partially identical thereto" means a nucleotide sequence obtained by substituting thymine with uracil in the nucleotide sequence of ORF or a nucleotide sequence partially identical thereto.

The sense strand consists of 15 to 25 nucleotides and preferably 19 nucleotides. The nucleotide sequence of the sense strand is desirably identical to the nucleotide sequence of ORF encoding LTβ. However, it may be a substantially identical (i.e., homologous) sequence. Specifically, the nucleotide sequence of a sense strand may comprise the ORF nucleotide sequence including a substitution, a deletion, an insertion, and/or an addition of 1 or a plurality of (i.e., 1 to 3) nucleotides, preferably 1 to 2 nucleotides, and more preferably 1 nucleotide.

The antisense strand has a nucleotide sequence that can hybridize to the sense strand under stringent conditions. The antisense strand may comprise a mismatch, including a substitution, a deletion, an insertion, and/or an addition of 1 to 3 nucleotides, preferably 1 or 2 nucleotides, and more preferably 1 nucleotide as long as it can hybridize under stringent conditions. Preferably, the antisense strand consists of a nucleotide sequence perfectly complementary to the sense strand.

The nucleotide sequences of a sense strand and an antisense strand can be selected based on a known nucleotide sequence encoding LTβ (Table 1). There are a variety of known methods for selecting such nucleotide sequences. For example, an siRNA Design Support System (Takara Bio Inc.) can be used.

A sense strand and an antisense strand are linked via a linker portion. The linker portion forms a loop such that the resulting strand is folded. Accordingly, the antisense strand and the sense strand hybridize to each other, resulting in formation of a double strand. Such a linker portion contained in a shRNA molecule is not particularly limited and thus it may be a polynucleotide linker or a non-polynucleotide linker as long as it links a sense strand and an antisense strand so as to form a stem loop structure. Preferably, a polynucleotide linker is the same consisting of 2 to 22 nucleotides known in the art. shRNA of the present invention can have an overhang comprising at least 2 nucleotides at the 3' end. For example, such overhang consists of a sequence comprising 1 to 5 nucleotides, preferably 1 to 3 nucleotides, and more preferably 1 or 2 nucleotides. Examples of a sequence include TTT, UU, and TT. Preferably, UU is used.

In some embodiments, the antisense nucleic acid is a short hairpin RNA (shRNA). In certain embodiments, the shRNA comprises a sense strand having the nucleotide sequence of CCGGCGAGAGGGTGTACGTCAACATCTCGAGATGTTGACGTACACCCTCTCGTTTTTG (SEQ ID NO: 11) and an antisense strand that hybridizes under stringent conditions to the sense strand. The shRNA described herein is capable of inhibiting expression of LTβ gene.

Peptides

The present disclosure is also based on the finding that LTβ interacts with EGFR and therefore enhances EGF-EGFR binding and to promote EGFR phosphorylation. LTβ may interact with the EGFR extracellular domain (EGFR-ECD), which increases EGF-EGFR binding and promotes EGFR dimerization and phosphorylation. LTβ may also interact with the EGFR intracellular domain (EGFR-ICD) to promotes EGFR phosphorylation. The Applicants found that interception of EGFR-LTβ interaction attenuates EGFR phosphorylation, resulting in sensitization of the resistant HNSCC cells to cetuximab treatment. Some peptides were found to be able to disrupt the interaction between LTβ and EGFR, reduce EGF-EGFR binding and EGFR phosphorylation, and successfully overcome the resistance to cetuximab in cancer cells.

Accordingly, another aspect of the present disclosure relates to a method of reducing or overcoming acquired resistance to cetuximab in a patient. The method described herein comprises administering to a patient a composition comprising a peptide. Examples of such peptides include, but are not limited to, QDGLYYLYCLVGYR (P-5) (SEQ ID NO:5), ERVYVNISH (P-9) (SEQ ID NO:9), or a combination thereof. Alternatively, the peptides can contain modified amino acid residues to improve in vivo stability following routine technology known in the art. The peptide may bind to the EGFR extracellular domain (EGFR-ECD) or the EGFR intracellular domain (EGFR-ICD).

Figure 5:
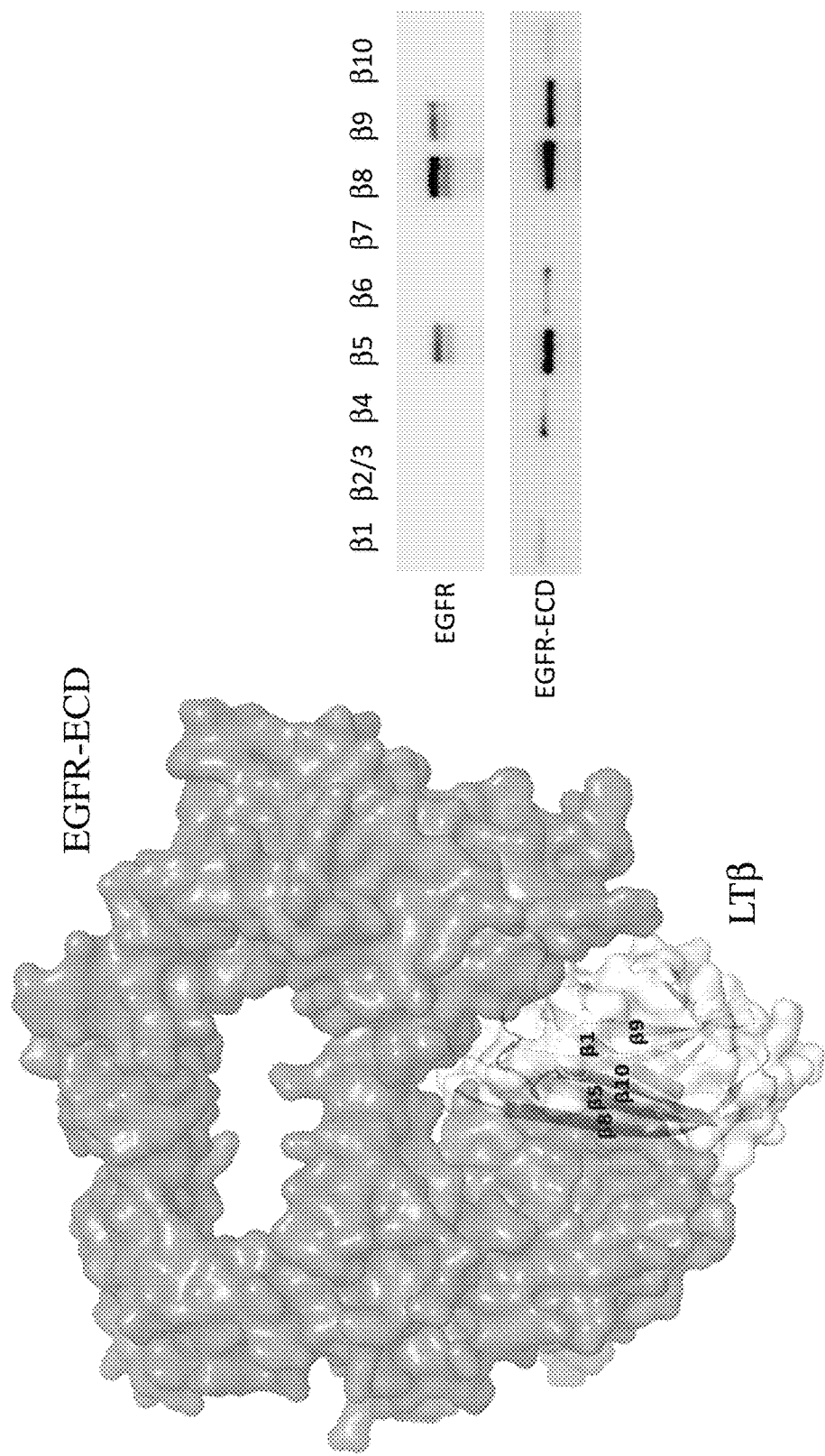
FIG. 5 shows the molecular docking of EGFR-ECD and LTβ, and the peptide binding assay. The purified full-length EGFR and EGFR-ECD was incubated with peptides containing sequences of different β-sheets of LTβ.

Human LTβ is composed of ten β-sheets. Computational simulation of molecular docking of EGFR and LTβ showed that the β-sheets of LTβ close to the D1 region of EGFR-ECD (FIG. 5), suggesting that the β-sheets of LTβ may serve as an interface for LTβ-EGFR interaction. Table 1 below shows the amino acid sequence of LTβ and the nucleic acid sequence of the gene encoding it.

TABLE 1

LTB lymphotoxin beta [Homo sapiens (human)]
NCBI-GeneID: 4050
Source: http://www.genome.jp/dbget-bin/www_bget?hsa:4050

Amino Acid Sequence (244 aa)
MGALGLEGRGGRLQGRGSLLLAVAGATSLVTLLLAVPITVLAVLALVPQD
QGGLVTETADPGAQAQQGLGFQKLPEEEPETDLSPGLPAAHLIGAPLKGQ
GLGWETTKEQAFLTSGTQFSDAEGLALPQDGLYYLYCLVGYRGRAPPGGG
DPQGRSVTLRSSLYRAGGAYGPGTPELLLEGAETVTPVLDPARRQGYGPL
WYTSVGFGGLVQLRRGERVYVNISHPDMVDFARGKTFFGAVMVG Nucleotide Sequence (735 nucleotides)
atgggggcactggggctggagggcagggtgggaggctccaggggagggg
ttccctcctgctagctgtggcaggagccacttctctggtgaccttgttgc
tggcggtgcctatcactgtcctggctgtgctggccttagtgccccaggat
caggggaggactggtaacggagacggccgacccgggggcacaggcccagca TABLE 1-continued

```
aggactggggtttcagaagctgccagaggaggagccagaaacagatctca
gccccgggctcccagctgcccacctcataggcgctccgctgaagggcag
gggctaggctgggagacgacgaaggaacaggcgtttctgacgagcgggac
gcagttctcggacgccgaggggctggcgctcccgcaggacggcctctatt
acctctactgtctcgtcggctaccggggccgggcgccccctggcggcggg
gacccccagggccgctcggtcacgctgcgcagctctctgtaccgggcggg
gggcgcctacgggccgggcactcccgagctgctgctcgagggcgccgaga
cggtgactccagtgctggacccggccaggagacaagggtacgggcctctc
tggtacacgagcgtggggttcggcggcctggtgcagctccggaggggcga
gagggtgtacgtcaacatcagtcaccccgatatggtggacttcgcgagag
ggaagaccttctttggggccgtgatggtggggtga
```

The present invention contemplates the design, production and uses of a number of LTβ peptides to disrupt the interaction between LTβ and EGFR. Nine peptides were synthesized and tested for the effect of intercepting LTβ-EGFR interaction in cetuximab-resistant cells. The amino acid sequences of nine peptides are listed in Table 2.

TABLE 2

| P1    | LPAAHLIGAPLKG  | SEQ ID NO: 2  |
| P2/3  | QGLGWETTKEQAFLT| SEQ ID NO: 3  |
| P4    | GTQFSDAEGLAL   | SEQ ID NO: 4  |
| P5    | QDGLYYLYCLVGYR | SEQ ID NO: 5  |
| P6    | QGRSVTLRSSLY   | SEQ ID NO: 6  |
| P7    | TPELLLEGAETVT  | SEQ ID NO: 7  |
| P8    | WYTSVGFGGLVQLR | SEQ ID NO: 8  |
| P9    | ERVYVNISH      | SEQ ID NO: 9  |
| P10   | KTFFGAVMVG     | SEQ ID NO: 10 |

P1 (SEQ ID NO: 2) represents the β-sheet of LTβ corresponding to residues 87 to 99 in SEQ ID NO:1

P2/3 (SEQ ID NO: 3) represents the β-sheet of LTβ corresponding to residues 100 to 114 in SEQ ID NO:1

P4 (SEQ ID NO: 4) represents the β-sheet of LTβ corresponding to residues 116 to 127 in SEQ ID NO:1

P5 (SEQ ID NO: 5) represents the β-sheet of LTβ corresponding to residues 129 to 142 in SEQ ID NO:1

P6 (SEQ ID NO: 6) represents the β-sheet of LTβ corresponding to residues 153 to 164 in SEQ ID NO:1

P7 (SEQ ID NO: 7) represents the β-sheet of LTβ corresponding to residues 174 to 186 in SEQ ID NO:1

P8 (SEQ ID NO: 8) represents the β-sheet of LTβ corresponding to residues 201 to 214 in SEQ ID NO:1

P9 (SEQ ID NO: 9) represents the β-sheet of LTβ corresponding to residues 217 to 225 in SEQ ID NO:1

P10 (SEQ ID NO: 10) represents the β-sheet of LTβ corresponding to residues 235 to 244 in SEQ ID NO:1

P1-P10 (SEQ ID NOs: 2-10) were tested for in vitro binding assay. Results showed that P5 (SEQ ID NO: 5), P8 (SEQ ID NO: 8) and P9 (SEQ ID NO: 9) interact with EGFR-ECD.

The $5^{th}$ β-sheet of LTβ having the amino acid sequence of QDGLYYLYCLVGYR (SEQ ID NO: 5) and the $9^{th}$ β-sheet of LTβ having the amino acid sequence of ERVYVNISH (SEQ ID NO: 9) of LTβ are capable for sensitizing cetuximab-resistant cells to cetuximab treatment.

The peptides described herein can be made by any conventional methods, i.e., recombinant technology or standard methods of solid phase peptide chemistry well known to any one of ordinary skill in the art. For example, the peptides may be synthesized by solid phase chemistry techniques following the procedures described by Steward et al. in Solid Phase Peptide Synthesis, 2nd Ed., Pierce Chemical Company, Rockford, Ill., (1984) using a Rainin PTI Symphony synthesizer. For solid phase peptide synthesis, techniques may be found in Stewart et al. in "Solid Phase Peptide Synthesis", W. H. Freeman Co. (San Francisco), 1963 and Meienhofer, Hormonal Proteins and Peptides, 1973, 2 46. For classical solution synthesis, see for example Schroder et al. in "The Peptides", volume 1, Acacemic Press (New York). In general, such methods comprise the sequential addition of one or more amino acids or suitably protected amino acids to a growing peptide chain on a polymer. Normally, either the amino or carboxyl group of the first amino acid is protected by a suitable protecting group. The protected and/or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

Any of the peptides (in isolated or synthesized form) described herein, as well as a composition (e.g., a pharmaceutical composition comprising the peptide and a pharmaceutically acceptable carrier), is also within the scope of the present disclosure. An isolated or synthesized peptide refers to a peptide or polypeptide substantially free from naturally associated molecules, i.e., the naturally associated molecules constituting at most 20% by dry weight of a preparation containing the polypeptide. Purity can be measured by any appropriate method, e.g., column chromatography, polyacrylamide gel electrophoresis, and HPLC.

The patient to be treated in the method described herein may have a tumor that has acquired resistance to cetuximab. The patient may be characterized by the absence of PIK3CA gene mutation, the absence of EGFR gene mutation, and/or the presence of wild-type RAS family genes (e.g. KRAS, HRAS, NRAS). In some embodiments, the patient is characterized by the absence of PIK3CA, KRAS, HRAS, NRAS, and EGFR gene mutation. In some embodiments, ERBB2 gene is not amplified in the tumor cells.

The method described herein may further comprise anti-EGFR antibody for treating cancer. The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

Cancer described herein includes, but is not limited to, head and neck cancer, head and neck squamous cell carcinoma (HNSCC), colorectal cancer, breast cancer, lung cancer, kidney cancer, thyroid cancer, brain cancer (glioma), ovarian cancer, pancreatic cancer, prostate cancer, plasma cell cancer (myeloma), liver cancer, muscle cancer (sarcoma), neuroblastoma, lymphoma, stomach cancer, adenoid cystic carcinoma, skin cancer including melanoma, basal cell carcinoma, or squamous cell carcinoma. In some embodiments, the cancer is a head and neck cancer, head and neck squamous cell carcinoma (HNSCC) or colorectal cancer. In some examples, the cancer can be a locally or regionally advanced HNSCC. Alternatively, the cancer can be a recurrent or metastatic HNSCC. In some embodiments, the cancer is a colorectal cancer.

Pharmaceutical Compositions and Therapy
Pharmaceutical Compositions

The present disclosure also relates to a pharmaceutical composition that comprises a combination of an anti-EGFR antibody and a composition described herein, and a pharmaceutically effective carrier.

The anti-EGFR antibody described herein can be an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

The composition described herein may be an agent that is an antagonist of Lymphotoxin-β (LTβ), in which the antagonist is an LTβ neutralizing antibody or an antisense nucleic acid such as a small hairpin RNA (shRNA), a small interfering RNA (siRNA) or a micro RNA (miRNA).

Preferable example of shRNA comprises a sense strand having the nucleotide sequence of CCGGCGAGAGGGT-GTACGTCAACATCTCGAGATGTTGACGTACAC-CCTCTCGTTTTT G (SEQ ID NO: 11) and an antisense strand that hybridizes under stringent conditions to the sense strand. The shRNA described herein is capable of inhibiting expression of LTβ gene.

The composition described herein may be a peptide. Examples of such peptides include, but are not limited to, QDGLYYLYCLVGYR (P-5) (SEQ ID NO:5), ERVYVNISH (P-9) (SEQ ID NO:9), or a combination thereof. Alternatively, the peptides can contain modified amino acid residues to improve in vivo stability following routine technology known in the art. The peptide may bind to the EGFR extracellular domain (EGFR-ECD) or the EGFR intracellular domain (EGFR-ICD).

One or more of the above-described peptides can be mixed with a pharmaceutically acceptable carrier (excipient), including buffer, to form a phaimaceutical composition for use in alleviating a hemophilia disorder. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the peptide described herein, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., a peptide described herein) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the peptide described herein, in which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. The peptides are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid prefonnulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 particularly 0.1 and 0.5 µm, and have a pH in the range of 5.5 to 8.0.

The emulsion compositions can be those prepared by mixing a peptide described herein with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner Use of Pharmaceutical Compositions for Therapy The present disclosure also relates to a method for treating cancer wherein the cancer is resistant to cetuximab, the method comprising administering a therapeutically effective amount of a pharmaceutical composition described herein to a patient suffering therefrom.

In some embodiments, the pharmaceutical composition described herein may comprise a combination of an anti-EGFR antibody and a peptide comprising comprises an amino acid sequence of QDGLYYLYCLVGYR (SEQ ID NO: 5). In some embodiments, the peptide described herein comprises an amino acid sequence of ERVYVNISH (SEQ ID NO: 9).

The anti-EGFR antibody described herein is an anti-EGFR antibody or an antigen binding fragment thereof. Examples of an anti-EGFR antibody include, but not limited to, cetuximab, MM-151, Sym004, matuzumab, panitumumab, zalutumumab, nimotuzumab and mAb 806. In some embodiments, the anti-EGFR antibody is cetuximab.

The patient to be treated in the method described herein can be a patient (e.g., a human patient) suffering from cancer, in particular, cancer resistant to anti-EGFR antibody (e.g., cetuximab). In some embodiments, the subject is a human cancer patient who has acquired resistance to cetuximab therapy.

The patient to be treated in any of the method described herein is a human patient suffering from cancer, in particular, cancer resistant to cetuximab. In some embodiments, the subject is a human cancer patient who is resistant to cetuximab therapy.

The patient to be treated in the method described herein may be characterized by the elevated expression level of LTβ, the absence of EGFR gene mutation, the absence of EGFR gene mutation, the absence of ERBB2 gene amplification, and/or the presence of wild-type RAS family genes.

In some embodiments, the patient to be treated by the method described herein may be characterized by increased Snail expression. In some embodiments, the patient may be characterized by increased LTβ expression. In some embodiments, the patient may be characterized by EGFR expression or overexpression with or without EGFR gene mutation (e.g. in exons 19-21). In some embodiments, the patient may be characterized by no mutation in EGFR. In some embodiments, the patient may be characterized by no mutation in PIK3CA. In some embodiments, the patient may be characterized by no mutation in RAS family genes. In some embodiments, the patient may be characterized by wild-type RAS family genes. In some embodiments, the patient may be characterized by no ERBB2 amplification.

In some embodiments, the methods described herein may further comprise administering at least one cytotoxic, chemotherapeutic, or anti-cancer agent to the patient.

In one example, the cancer is a metastatic colorectal cancer.

Examples of anti-cancer agents include, but are not limited to, alkylating agents or agents with an alkylating action, such as, for example, cyclophosphamide (CTX; e.g. CYTOXAN®), chlorambucil (CHL; e.g. LEUKERAN®), cisplatin (C is P; e.g. PLATINOL®), oxaliplatin (e.g. ELOXATIN™), busulfan (e.g. MYLERAN®), melphalan, carmustine (BCNU), streptozotocin, triethylenemelamine (TEM), mitomycin C, and the like; anti-metabolites, such as, for example, methotrexate (MTX), etoposide (VP16; e.g. VEPESID®), 6-mercaptopurine (6 MP), 6-thioguanine (6TG), cytarabine (Ara-C), 5-fluorouracil (5-FU), capecitabine (e.g. XELODA®), dacarbazine (DTIC), and the like; antibiotics, such as, for example, actinomycin D, doxorubicin (DXR; e.g. ADRIAMYCINS), daunorubicin (daunomycin), bleomycin, mithramycin and the like; alkaloids, such as, for example, vinca alkaloids such as, for example, vincristine (VCR), vinblastine, and the like; and other antitumor agents, such as, for example, paclitaxel (e.g. TAXOL®) and paclitaxel derivatives, the cytostatic agents, glucocorticoids such as dexamethasone (DEX; e.g. DECADRON®) and corticosteroids such as, for example, prednisone, nucleoside enzyme inhibitors such as, for example, hydroxyurea, amino acid depleting enzymes such as, for example, asparaginase, leucovorin, folinic acid, raltitrexed, and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, cladribine, camptothecin, 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, or chlorambucil.

The use of the cytotoxic, chemotherapeutic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

Another aspect of the present disclosure relates to a method of inhibiting the growth of EGFR-expressing tumor cells that are resistant to cetuximab therapy, the method comprising contacting the tumor cells with an effective amount of a combination of anti-EGFR antibody and a composition. The composition may comprise an agent that is an antagonist of Lymphotoxin-β (LTβ), in which the antagonist is an LTβ neutralizing antibody or an antisense nucleic acid such as a small hairpin RNA (shRNA), a small interfering RNA (siRNA) or a micro RNA (miRNA).

Preferable example of shRNA is a single strand RNA of the nucleotide sequence: CCGGCGAGAGGGTGTACGTCAACATCTCGAGATGTTGACGTACACCCTCTCGTTTTTG (SEQ ID NO: 11).

The composition may comprise a peptide comprising comprises an amino acid sequence of QDGLYYLYCLVGYR (SEQ ID NO: 5). In some embodiments, the peptide described herein comprises an amino acid sequence of ERVYVNISH (SEQ ID NO: 9).

Cancer described herein includes, but is not limited to, head and neck cancer, head and neck squamous cell carcinoma (HNSCC), colorectal cancer, breast cancer, lung cancer, kidney cancer, thyroid cancer, brain cancer (glioma), ovarian cancer, pancreatic cancer, prostate cancer, plasma cell cancer (myeloma), liver cancer, muscle cancer (sarcoma), neuroblastoma, lymphoma, stomach cancer, adenoid cystic carcinoma, skin cancer including melanoma, basal cell carcinoma, or squamous cell carcinoma. In some embodiments, the cancer is a head and neck cancer, head and neck squamous cell carcinoma (HNSCC) or colorectal cancer. In some examples, the cancer can be a locally or regionally advanced HNSCC. Alternatively, the cancer can be a recurrent or metastatic HNSCC. In some embodiments, the cancer is a colorectal cancer.

To practice the method disclosed herein, an effective amount of any of the pharmaceutical compositions described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the peptides described herein can be aerosolized using a fluorocarbon formulation and a metered dose inhaler, or inhaled as a lyophilized and milled powder.

Empirical considerations, such as the half-life, generally will contribute to the determination of the dosage. Frequency of administration may be determined and adjusted over the course of therapy, and is generally, but not necessarily, based on treatment of the cancer. Alternatively, sustained continuous release formulations of a peptide may be appropriate. Various formulations and devices for achieving sustained release are known in the art.

In one example, dosages for a peptide as described herein may be determined empirically in individuals who have been given one or more administration(s) of the peptide.

Generally, for administration of any of the peptide described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate the hemophilic disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/kg to about 2 mg/kg (such as about 3 μg/kg, about 10 μg/kg, about 30 μg/kg, about 100 μg/kg, about 300 μg/kg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

A pharmaceutical composition comprising a peptide as described herein may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a peptide will depend on the specific peptide (or compositions thereof) employed, the type and severity of the cancer, previous therapy, the patient's clinical history and response to the peptide, and the discretion of the attending physician. Typically the clinician will administer a peptide until a dosage is reached that achieves the desired result. Administration of a peptide can be continuous or intermittent, depending, for example, upon the recipient's physiological condition, and other factors known to skilled practitioners. The administration of a peptide may be essentially continuous over a preselected period of time or may be in a series of spaced dose.

In some embodiments, conventional methods, known to those of ordinary skill in the art of medicine, can be used to administer the pharmaceutical composition to the subject, depending upon the type of cancer to be treated. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble polypeptide can be administered by the drip method, whereby a pharmaceutical formulation containing the polypeptide and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a phannaceutical excipient such as Water-for-Injection, 0.9% saline, or 5% glucose solution.

Kits

Also encompassed by the present disclosure are kits (e.g., phamiaceutical packs). The inventive kits may be useful for treating cancer or drug-resistant cancer (e.g., cetuximab-resistant cancer). Such kits can include one or more containers comprising a peptide as described herein or a pharmaceutical composition described herein.

In some embodiments, the kit can comprise instructions for use in accordance with any of the methods described herein. The included instructions can comprise a description of administration of the peptide or the pharmaceutical composition to treat cancer or drug-resistant cancer (e.g., cetuximab-resistant cancer) according to any of the methods described herein. The kit may further comprise a description of selecting an individual suitable for treatment based on identifying whether that individual has a drug-resistant cancer (e.g., cetuximab-resistant cancer). In still other embodiments, the instructions comprise a description of administering a peptide as described herein or a pharmaceutical composition described herein to an individual at risk of drug-resistant cancer (e.g., cetuximab-resistant cancer).

The instructions relating to the use of a peptide generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating or alleviating a drug-resistant cancer (e.g., cetuximab-resistant cancer). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a peptide such as SEQ ID NO:5 or 9.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Definitions

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

As used herein, the term "peptide" refers to an amino acid sequence from 2 amino acids to 50 amino acids. Preferably, the peptide comprises from 3 amino acids to 45 amino acids, more preferably from 3 to 40 amino acids, even more preferably from 4 to 30 amino acids. Particularly preferred embodiments include peptides comprising from 4 to 20 amino acids, such as from 5 to 15 amino acids or from 5 to 10 amino acids. As used herein, "amino acids" are represented by their full name, their three letter code or their one letter code as well known in the art. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. The term "amino acids" includes both natural and synthetic amino acids, and both D and L amino acids. "Standard amino acid" or "naturally occurring amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl.

As used herein, "amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The peptides of the invention may comprise naturally standard amino acids or nonstandard amino acids. Peptidemimetics include peptides having the following modifications: i) peptides wherein one or more of the peptidyl —C(O)NR linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) peptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or C$_1$-C$_4$ alkyl with the proviso that R and R$^1$ are not both hydrogen; iii) peptides wherein the C teiminus is derivatized to —C(O)R$^2$ where R$^2$ is selected from the group consisting of C$_1$-C$_4$ alkoxy, and —NR$^3$R$^4$ where R$^3$ and R$^4$ are independently selected from the group consisting of hydrogen and C$_1$-C$_4$ alkyl.

As used herein, the term "conservative amino acid substitution" is defined herein as an amino acid exchange within one of the following five groups:

I. Small aliphatic, nonpolar or slightly polar residues: Ala, Ser, Thr, Pro, Gly;

II. Polar, negatively charged residues and their amides: Asp, Asn, Glu, Gln;

III. Polar, positively charged residues: His, Arg, Lys;

IV. Large, aliphatic, nonpolar residues: Met, Leu, Be, Val, Cys

V. Large, aromatic residues: Phe, Tyr, Trp.

The terms "administer," "administering," or "administration," as used herein refers to implanting, absorbing, ingesting, injecting, inhaling, or otherwise introducing an inventive pharmaceutical composition described herein.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The terms "ErbB 1", "epidermal growth factor receptor" and "EGFR" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB 1 refers to the gene encoding the EGFR protein product. As used herein, the EGFR protein is disclosed as GenBank accession no. NP-005219 (SEQ ID NO: 1) which is encoded by the erbBl gene, GenBank accession no. NM-005228 (SEQ ID NO: 2).

The term "RNA interference" or "RNAi" refers to the silencing or decreasing of gene expression by RNAi agents (e.g., "short interfering RNA", "siRNA", "shRNA", "short interfering nucleic acid molecule", "short interfering oligonucleotide molecule", or "chemically-modified short interfering nucleic acid molecule"). The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference (see, e.g., (Grimm, Adv. Drug Deliv. Rev., 61, 672, 2009; Gondi, J. Cell Physiol, 220, 285, 2009; Carthew, 136, 642, 2009; Jinek, 457, 405, 2009; Ghildiyal, Nat. Rev. Genet., 10, 94, 2009). RNAi is the process of sequence-specific, post-transcriptional gene silencing in cells, animals and plants, initiated by an RNAi agent that is homologous in its duplex region to the sequence of the to-be-silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be completely or partially inhibited.

In some embodiments, the RNAi agent can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The RNAi agent can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the RNAi agent is assembled from a single oligonucleotide, where the self-complementary sense and antisense regions of the RNAi agent are linked by means of a nucleic-acid-based or non-nucleic acid-based linker(s). The RNAi agent can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The RNAi agent can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active small nucleic acid molecule capable of mediating RNAi. The RNAi agent can also comprise a single stranded polynucleotide having nucleotide sequence complementary to nucleotide sequence in a target nucleic acid molecule or a portion thereof. For present purposes, RNAi agent molecules need not be limited to those molecules containing only naturally occurring RNA, but further encompasses chemically-modified nucleotides and non-nucleotides.

The term "RNAi agent" is meant to be equivalent to other term's used to describe nucleic acid molecules that are capable of mediating sequence specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics. As used herein, "siRNA" frequently refers to artificial nucleotide sequences that are used in RNA interference therapy. Typically, an siRNA is a double-stranded nucleic acid molecule comprising two nucleotide strands, each strand having about 19 to about 28 nucleotides.

A short hairpin RNA (shRNA) is a sequence of RNA that makes a tight hairpin turn that can be used to silence gene expression via RNA interference. It is typical to use a vector to introduce shRNA into cells and to use a promoter (e.g., the U6 promoter) to ensure that the shRNA is expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

MicroRNAs (miRNAs) are a class of endogenous, single or double-stranded, about 22 nucleotide-long RNA molecules that regulate as much as 30% of mammalian genes, with important roles in regulation of cellular differentiation, proliferation, and apoptosis. Specific patterns of up- and down-regulation of miRNAs in various human tumor types are recognized. miRNA represses protein production by blocking translation or causing transcript degradation.

The terms "gene knockdown", "knockdown", or "knockdown" are used interchangeably and refer to techniques by which the expression of one or more of an organism's genes is reduced, either through genetic modification (a change in the DNA of one of the organism's chromosomes) or by treatment with a reagent such as a short DNA or RNA oligonucleotide with a sequence complementary to either an mRNA transcript or a gene. Knockdown using RNAi agents changes gene expression through, inter alia, degradation of the mRNA, blocking of the mRNA translation, or blocking maturation of pre-mRNA to mRNA.

The terms "siRNA against (name of a gene)", "anti-(name of a gene) siRNA" are used interchangeably and refer to an siRNA that is directed at a gene for the purpose of silencing the gene.

The terms "expression" and "transfection" of the RNAi agents are used interchangeably, and refer to the activity of the RNAi agents after delivery inside the cell. A high expression or transfection indicates effective knockdown of the target protein or proteins. For siGLO, a green-fluorescent dsRNA molecule designed to be transported to the nucleus after delivery to the cytosol of a cell and after release from the vectors or endosomes as a free molecule, expression or transfection is indicated by the accumulation of green fluorescence in the nucleus of the cell.

Within certain embodiments of this disclosure, pharmaceutical compositions and methods are provided that feature the presence or administration of one or more RNAi molecules or other dsRNA or analogs thereof of this disclosure, possibly combined, complexed, or conjugated with a polypeptide, optionally formulated with a pharmaceutically-acceptable carrier, such as a diluent, stabilizer, buffer, or the like. The negatively charged dsRNA molecules of this disclosure may be administered to a patient by any standard means, with or without stabilizers, buffers, or the like, to form a composition suitable for treatment. When it is desired to use a liposome delivery mechanism, standard protocols for formation of liposomes can be followed. The compositions of the present disclosure may also be formulated and used as a tablet, capsule or elixir for oral administration, suppository for rectal administration, sterile solution, or suspension for injectable administration, either with or without other compounds known in the art. Thus, dsRNAs of the present disclosure may be administered in any form, such as nasally, transdermally, parenterally, or by local injection.

The terms "cancer", "tumor cell" and "tumor" are used interchangeably and refer to any neoplasm ("new growth"), such as, for example, a carcinoma (derived from epithelial cells), adenocarcinoma (derived from glandular tissue), sarcoma (derived from connective tissue), lymphoma (derived from lymph tissue), or cancer of the blood (e.g., leukemia or erythroleukemia). The terms "cancer" or "tumor cell" also are intended to encompass cancerous tissue or a tumor mass, which shall be construed as a compilation of cancer cells or tumor cells, and are intended to encompass cancers or cells that may be either benign, premalignant, or malignant. Typically a cancer or tumor cell exhibits various art recognized hallmarks such as, for example, growth factor independence, lack of cell/cell contact growth inhibition, and/or abnormal karyotype. By contrast, a normal cell typically can only be passaged in culture for a finite number of passages and/or exhibits various art-recognized hallmarks attributed to normal cells (e.g., growth factor dependence, contact inhibition, and/or a normal karyotype). Genetically normal cells that are physically part of the aberrant growth and frequently play an integral role in the proliferative process are also referred to as cancer cells or tumor cells. This includes, inter alia, stromal and endothelial cells that proliferate under influence of tumor-secreted factors, and stromal cells that stimulate proliferation of epithelial tumor cells.

The term "cell" includes any eukaryotic cell, such as, for example, somatic or germ line mammalian cells, or cell lines, e.g., HeLa cells (human), NIH3T3 cells (murine), embryonic stem cells, and cell types such as hematopoietic stem cells, myoblasts, hepatocytes, lymphocytes, and epithelial cells and, e.g., the cell lines described herein.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

A "neutralizing antibody" may inhibit or reduce the levels of LTβ in a cell. The inhibitory concentration of the monoclonal antibody may be less than about 25 mg/ml to neutralize about 50% of the target molecule levels in a cell.

As used herein, the term "antigen" is defined as any substance capable of eliciting an immune response.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The ten "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLES

In order that the invention described herein may be more fully understood, the following examples are set forth. It should be understood that these examples are for illustrative purposes only and are not to be construed as limiting this invention in any manner.

Example 1: Generation of Cetuximab-Resistant HNSCC Cells

Establishment of in vitro-selected cetuximab resistant cell line OECM1-Ctx$^R$

Figure 1:
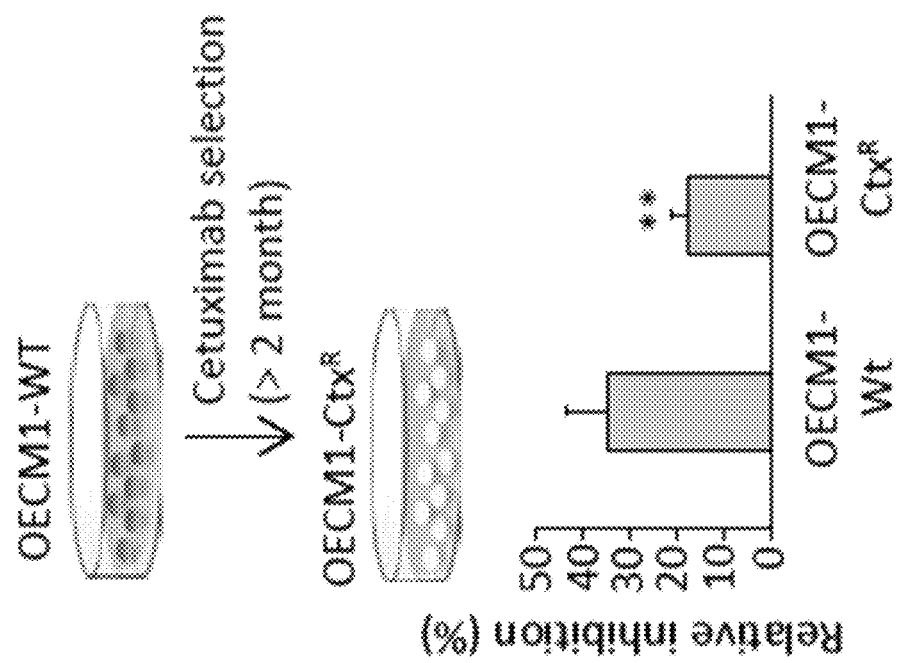
FIG. 1 illustrates the procedure of generating cetuximab-resistant OECM1 cells (OECM1-Ctx$^R$), and the relative growth inhibition by cetuximab for OECM1 and OECM1-Ctx$^R$ cells. Data represent mean±S.D. n=3. **P<0.01 (Student's t test).

A cetuximab-resistant HNSCC cell line (named OECM1-Ctx$^R$) was generated by continuous treatment of OECM1 cells (starting from the concentration of IC$_{50}$ of OECM1 at 200 μg/ml) with cetuximab (300 ng/ml) for 2-3 months until cells proliferate freely. A growth curve was used to determine the resistance of the generated cetuximab-resistant subline OECM1-Ctx$^R$. In comparison with OECM1 parental cells, the OECM1-Ctx$^R$ subline revealed a lower inhibition rate by cetuximab (FIG. 1).

Establishment of In Vivo-Selected Cetuximab Resistant Cell Line FaDu-Ctx$^R$

Figure 2A:
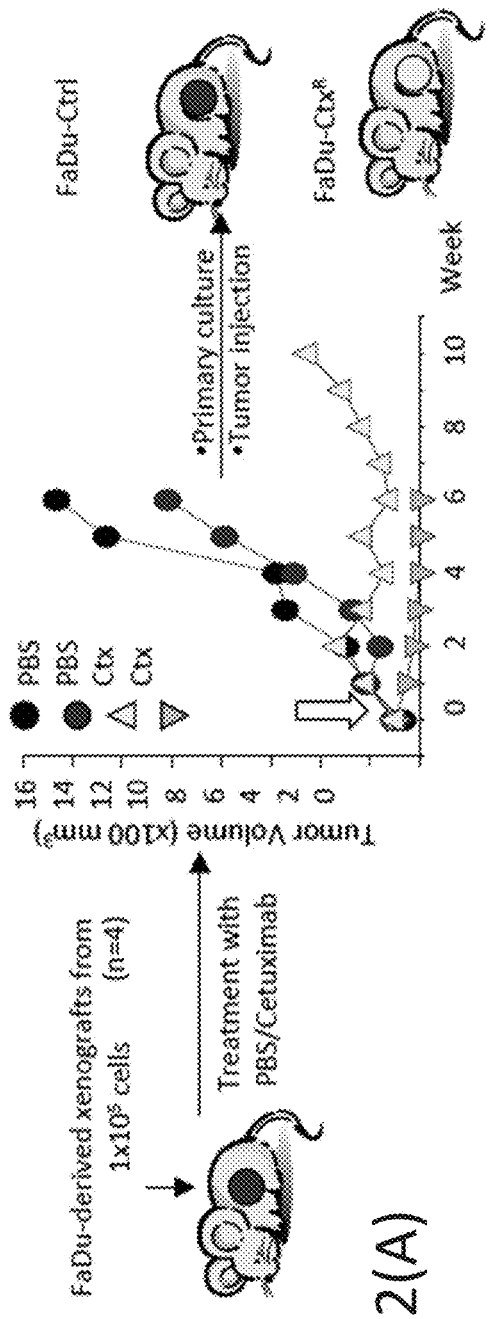
FIGS. 2(A)-(B). (A) illustrates the generation of in vivo-selected FaDu-Ctx$^R$ cells. (B) illustrates the in vivo validation of the cetuximab resistance of FaDu-Ctx$^R$ and FaDu-ctrl. The above sublines were inoculated into the subcutaneous area of nude mice and treated with cetuximab (ctx), and FaDu-ctrl treated with PBS was applied as a control. Left, the relative tumor volume of the mice. Right, a photo for showing the xenotransplanted tumors. Scale bar=1 cm.
Figure 2B:
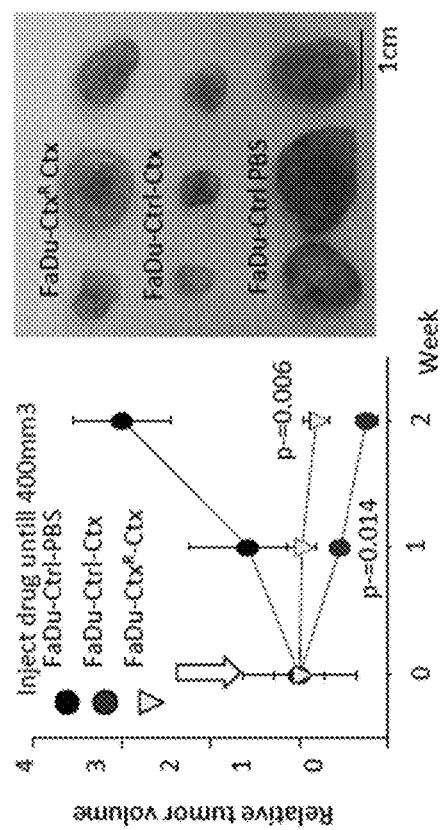
Figure 3:
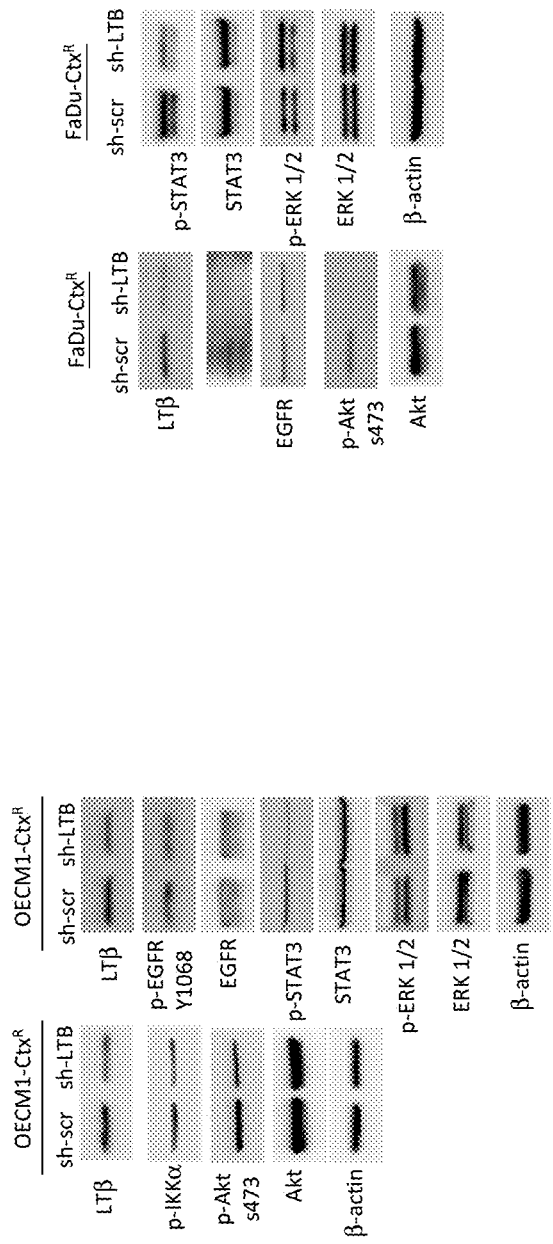
FIG. 3 shows the western blots indicating the knockdown of LTβ by shRNA reverses cetuximab resistance for OECM1-Ctx$^R$ and FaDu-Ctx$^R$ cells.
Figure 4:
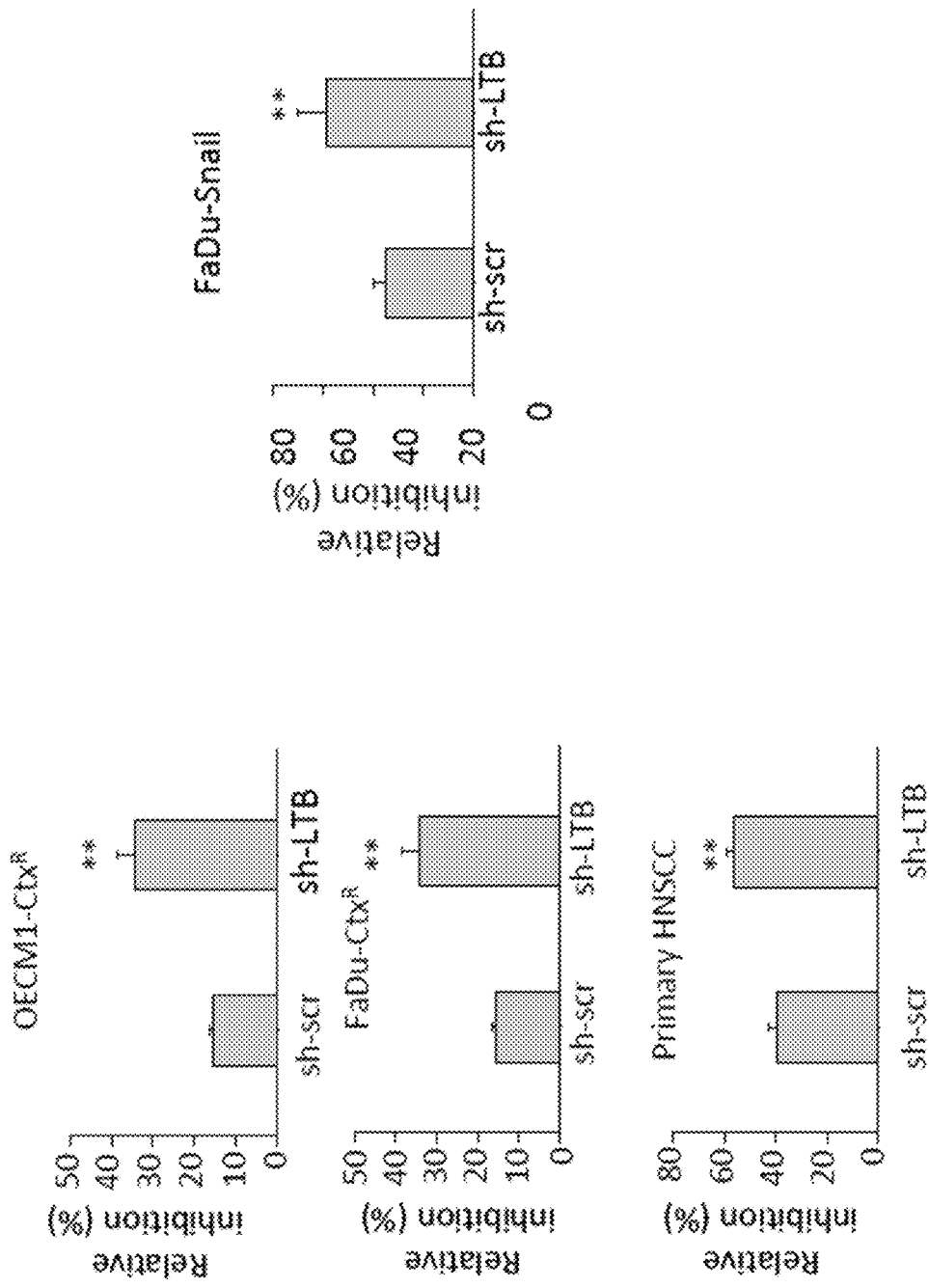
FIG. 4 shows the relative growth inhibition by cetuximab for OECM1-Ctx$^R$ and FaDu-Ctx$^R$ cells receiving a shRNA against LTβ or a control sequence.

A cetuximab-resistant HNSCC subline (named FaDu-Ctx$^R$) was established by in vivo selection. 1×10$^5$ wild-type FaDu cells per mouse were inoculated into the subcutaneous area of Balb/c nude mice (n=4). Two mice were treated with PBS and two were treated with cetuxmab once a week. Among the two cetuximab-treated mice, a total tumor shrinkage wad noted in one, and another mouse showed persistent tumor growth. After 10 weeks, the xenograpfted tumor was harvested for primary culture. Two sublines were established: control subline FaDu-control from PBS-treated group, and cetuximab-resistant subline FaDu-Ctx$^R$ from cetuximab treatment group. The resistance of FaDu-Cxt$^R$ was confirmed in vivo and in vitro. Subsequently, these two sublines were inoculated into nude mice again and treated with cetuximab. The persistence of tumors was only shown in FaDu-Ctx$^R$ but not in FaDu-control (FIG. 2).

Example 2: Role of Snail-Induced EMT in HNSCC Cetuximab Resistance

OECM1-Ctx$^R$ harbors a mesenchymal-like phenotype including a fibroblatoid morphology and changes of EMT markers. Gene set enrichment analysis (GSEA) demonstrated a significant correlation between the EMT core signature and cetuximab resistance, revealing the association between acquired resistance of cetuximab and EMT in HNSCC. Among the EMT regulators, Snail was found to be a major regulator that mediates cetuximab resistance, and was shown to be upregulated significantly in OECM1-Ctx$^R$. Knocking down of Snail in OECM1-Ctx$^R$ attenuated the cetuxmab resistance. Upregulation of Snail was found in FaDu-Ctx$^R$ by western blot. To confirm the role of Snail in cetuximab resistance, Snail was stably transfected into FaDu cells (FaDu-Snail) and the inhibitory effect of cetuximab on FaDu-Snail versus a control clone was analyzed. The result showed the ectopic Snail reduced the inhibitory effect. In contrast, overexpression of Twist1 did not correlate with the cetuximab-resistance signature. In HNSCC patients developing resistance to cetuximab after treatments, the level of SNAI1 expression was increased. The result indicates that Snail-induced EMT plays an important role in HNSCC cetuximab resistance.

Example 3: Acquired Resistance to Cetuximab is Independent from Driver Genes Mutations The driver genes, PIK3CA, EGFR, RAS family genes (KRAS, HRAS, NRAS), and ERBB2, are known to be involved in cetuximab resistance. In head and neck squamous cell carcinoma (HNSCC), the incidence of RAS mutation, which is the major cause of cetuximab resistance, is relatively rare compared with the other types of cancers, and the mechanism mediating acquired resistance is unclear compared to the driver gene mutation-mediated de novo resistance.

To investigate the mechanism that mediates Cetuximab acquired resistance, direct sequencing of the driver genes (PIK3CA, KRAS, HRAS, NRAS, and EGFR) and ERBB2 amplification was performed in two resistant sublines (FaDu-Ctx$^R$ and OECM1-Ctx$^R$) and samples from two patients (Patient 1 and Patient 2) that developed cetuximab resistance after treatment. No gene mutation or ERBB2 amplification was found in these samples.

Table 1 summarizes the result of sequencing. (ND, not detected).

| Gene | Mutation | OECM1-Ctx$^R$ | FaDu-Ctx$^R$ | Patient 1 | Patient 2 |
|---|---|---|---|---|---|
| PIK3CA | Exon 9/20 | ND | ND | ND | ND |
| KRAS | Codon 12/13/61/146 | ND | ND | ND | ND |
| HRAS | Codon 12/13/62 | ND | ND | ND | ND |
| NRAS | Codon 12/13/61 | ND | ND | ND | ND |
| EGFR | Exon 18/19/20/21 and T790 | ND | ND | ND | ND |
| ERBB2 | Amplification | ND | ND | ND | ND |

The result of sequencing indicates that the acquired resistance of cetuximab is not related to the mutation of the driver genes (PIK3CA, KRAS, HRAS, NRAS, and EGFR) and EGFR expression. Furthermore, the expression levels of surface EGFR for OECM1-CtxR and the parental cells have no difference. Collectively, the results reveal that Snail is crucial in the development of acquired resistance to cetuximab in HNSCC, and the acquired resistance is independent from the known driver genes mutations.

Example 4: LTβ Mediates Acquired Resistance to Cetuximab in HNSCC

The "core signature for cetuximab resistance" was obtained by intersection of the upregulated genes obtained from microarray of OECM1-Ctx$^R$ versus OECM1 parental cells with the genes from RNA-seq data for cetuximab resistance (GSE21483). The core signature for cetuximab resistance was intersected with the signature from RNA-seq for FaDu-Snail/FaDu-vector. RNA-seq was performed in FaDu-Snail vs. FaDu-vector control, and 396 Snail-upregulated genes were found to be closely related to the cetuximab-resistance signature. Among the upregulated genes, LTB which encodes lymphotoxin-β (LTβ) was top-ranked in both cetuximab-resistant cells and Snail-overexpressed cells. LTβ was also upregulated in OECM1-Ctx$^R$ cells. The result showed that the expression level of LTβ was increased in both cetuximab resistant sublines OECM1-Ctx$^R$ and FaDu-Ctx$^R$. Consistently, a higher expression of LTB was demonstrated in samples obtained from patients who developed cetuximab resistance after treatment (FIG. 11). Knockdown of LTβ increased cetuximab sensitivity in both OECM1-Ctx$^R$ and FaDu-Ctx$^R$, and sensitized the primary HNSCC cells obtained from a cetuximab resistance patient. A positive correlation between the expression of SNAP and LTB was demonstrated both in 58 HNSCC samples from Taipei Veterans General Hospital and in 542 HNSCC samples from TCGA database. A positive correlation between Snail and LTβ was also noted in HNSCC cell lines. Ectopic expression of Snail upregulated LTβ whereas knockdowon of Snail suppressed LTβ. Induction of Snail expression by TGF-β treatment in OECM1 cells upregulated LTβ expression. Furthermore, knocking down LTβ in FaDu-Snail attenuated Snail-induced cetuximab resistance. Knocking down LTβ in OECM1-Ctx$^R$ reversed the mesenchymal penotype, and overexpression of LTβ in FaDu promoted EMT. Taken together, the findings reveal that LTβ is a key for mediating Snail-induced Cetuximab resistance in HNSCC.

Example 5: LTβ Activates NF-κB Signal Pathways in Cetuximab-Resistant HNSCC Through EGFR-Akt-IKKα Pathway Activation of NF-κB in cetuximab-resistant cells was evident by an increased expression of nuclear p65 and p52 proteins and an enhanced NF-κB activity. Knockdown of LTB reduced nuclear p65 and p52, and suppression of LTB by either shRNA or a LTβ neutralizing antibody reduced NF-κB reporter activity.

LTβ neutralizing antibody used in the study was purchased from LifeSpan BioSciences, Inc. (Product number: LS-C118993). shRNA has the sequence of CCGGCGAGAGGGTGTACGTCAACATCTCGAGATGTTGACGTACACCCTCTCGTTTTT G (SEQ ID NO: 11)

Knockdown of LTβ also attenuated the expression of both canonical and non-canonical NF-κB target genes. Inhibition of NF-κB activity by parthenolide or the proteosomal inhibitor bortezomib sensitized OECM1-Ctx$^R$ or primary HNSCC cells to cetuximab treatment. Because TNFα is an important target of NF-κB pathway and TNFα maintains Snail acetylation for activating target gene trnascription, the applicants examined whether cetuximab-resistant cells secrete a higher level of TNFα for maintaining the acetyl Snail-LTβ signal. An increased TNFα level was found in the supernatant of OECM1-Ctx$^R$ compared with the parental OECM1, and blocking LTβ by the neutralizing antibody suppressed TNFA expression.

The expression of LTα and LTβ in cetuximab-resistant cells was examined. The expression of LTβ and LTβR was evident in OECM1-Ctx$^R$; in contrast, OECM1-Cxt$^R$ barely expressed LTα. The applicants therefore considered that LTβ activates NF-κB through an LTα/LTβR-independent pathway in cetuximab-resistant cells. Because constitutive activation of EGFR is frequently noted in anti-EGFR resistant cancer cells and Akt, a major downstream kinase of EGFR, has been shown to induce NF-κB activation through directly phosphorylating IKKα[32] or mTOR-mediated mechanism[33], we examined whether EGFR-mediated Akt activation is responsible for NF-κB activation in cetuximab-resistant HNSCC cells. The result showed that an increased level of EGFR phosphorylation at tyrosine 845, 1068, and 1086 was shown in both resistant sublines, and a higher level of phosphorylated Akt, IKKα and Stat3 was also noted, which suggests that the EGFR-Akt-IKKα-NF-κB pathway is activated in Cetuximab-resistant cells. Interestingly, knocking down LTβ in two resistant sublines inhibited the above pathway at the level of EGFR phosphorylation, suggesting the crosstalk between LTβ and the EGFR-Akt-IKKα-NF-κB pathway Inhibition of EGFR activity sensitized OECM1-Ctx$^R$ and the primary HNSCC cells to cetuximab treatment, and the EGFR tyrosine kinase inhibitor showed an additive effect to cetuximab. Together, the results suggest that LTβ activates NF-κB through EGFR-Akt-IKKα pathway.

Example 6: A Combinatory Effect of Afatinib and Bortezomib in Cetuximab-Resistant HNSCC Cells Since LTβ β-activated EGFR and NF-κB pathways are both important for cetuximab resistance, the applicants examined whether combining two clinically-used drugs, the EGFR tyrosine kinase inhibitor afatinib and the protesome inhibitor bortezimb which is considered as a NF-κB inhibitor[34], will be more effective. Combination of afatinib and bortezomib provided a higher inhibitory effect for both resistant sublines (FIG. 1), and a synergistic effect of afatinib and bortezomib was demonstrated in vitro. The applicants next applied the zebrafish model for confirming their synergy in vivo. One hundred labelled OECM1-Ctx$^R$ cells were injected into the two-day-old zerafish embryo. The embryo were treated with different combination of drugs one day after injection, and the tumor cells were observed and recorded one day (baseline) or three day after tumor cells injection. The result showed that a significantly increased inhibitory effect on OECM1-Ctx$^R$ proliferation was shown in the afatinib plus bortezomib group compared with afatinib alone or afatinib combined with other drugs. These data indicate a synergistic effect of afatinib and bortezomib in cetuximab-resistant HNSCC cells.

Example 7: LTβ Interacts with EGFR to Enhance EGFR-Ligand Binding and to Promote EGFR Phosphorylation To investigate the mechanism of LTβ-induced EGFR, the applicants first examined whether LTβ interacts with EGFR. In FaDu-Ctx$^R$ cells, the endogenous LTβ interacted with EGFR. A proximity ligation assay confirmed the interaction between LTβ and total/phosphorylated EGFR in another cetuximab-resistant subline OECM1-Ctx$^R$. Ectopic LTβ interacted with EGFR. Intringuingly, LTβ interacted with both the extracellular domain (ECD) and intracellular domain (ICD) of EGFR. The applicants therefore examined the localization of LTβ in cetuximab-resistant cells. In OECM1-Ctx$^R$, LTβ expressed ubiquitously at the plasma membrane, cytoplasm, and nucleus. According to these results, the applicants assumed that the overexpressed LTβ in cetuximab-resistant cells located at both surface membrane and cytoplasm, which may interact with the corresponding parts of EGFR, i.e., ECD and ICD. First, the applicants investigated the effect of LTβ on EGFR ligand binding. A significantly reduced EGFR ligand binding was shown in OECM1-Ctx$^R$ cells compared with the OECM1 parental cells. A reduced dissociation constant (Kd) for EGFR ligand binding was noted when transfected with LTβ. Since ligand-induced EGFR dimerization is resposible for EGFR activation[35], the applicants further examined whether LTβ affects EGFR dimerization to influence EGFR activation. An increased EGFR dimerization was shown in OECM1-Ctx$^R$ cells in the absence of EGF treatment. Mutation of EGFR lysine 721, a ATP binding site[36], but not valine 924, a critical site mediatng the formation of EGFR dimer[37], inhibited LTβ-induced EGFR dimerization. Furthermore, LTβ also promoted EGFR-ICD phosphorylation in vitro. In summary, the above data indicates that LTβ interacts with EGFR-ECD, which increases EGFR ligand binding to promote EGFR dimerization and phosphorylation; LTβ also interacts with EGFR-ICD to promotes EGFR phosphorylation.

Example 8: Effect of Intercepting LTβ-EGFR Interaction in Cetuximab-Resistant Cells Structurally, LTβ is composed of ten β-strands (β1-β10). Computational simulation of molecular docking of EGFR and LTβ showed that the β-sheets of LTβ close to the D1 region of EGFR-ECD, suggesting that the β-sheets of LTβ may serve as an interface for LTβ-EGFR interaction.

Nine peptides were synthesized with the sequences of LTβ β-strands for investigating the effect of intercepting LTβ-EGFR interaction in cetuximab-resistant cells. The amino acid sequences of nine peptides are listed in Table 2.

TABLE 2

| P1 | LPAAHLIGAPLKG | SEQ ID NO: 2 |
| P2/3 | QGLGWETTKEQAFLT | SEQ ID NO: 3 |
| P4 | GTQFSDAEGLAL | SEQ ID NO: 4 |
| P5 | QDGLYYLYCLVGYR | SEQ ID NO: 5 |
| P6 | QGRSVTLRSSLY | SEQ ID NO: 6 |
| P7 | TPELLLEGAETVT | SEQ ID NO: 7 |
| P8 | WYTSVGFGGLVQLR | SEQ ID NO: 8 |
| P9 | ERVYVNISH | SEQ ID NO: 9 |
| P10 | KTFFGAVMVG | SEQ ID NO: 10 |

The applicants examined the effect of treating the peptides containing different β-sheets of LTβ on OECM1-Ctx$^R$. Both 5$^{th}$ and 9$^{th}$ β-sheet of LTβ suppressed EGFR Y1068 phosphorylation, and the 9$^{th}$ β-sheet had a more prominent effect. The 9$^{th}$ β-sheet of LTβ inhibits EGFR dimerization in OECM1-Ctx$^R$. Furthermore, the 9$^{th}$ β-sheet also reduced EGF-EGFR binding (FIG. 5), and the 5$^{th}$ and 9$^{th}$ β-sheets of LTβ sensitized OECM1-Ctx$^R$ to cetuximab treatment.

Since LTβ also induces EGFR-ICD phosphorylation in vitro, the applicant also investigated whether interception of EGFR-ICD and LTβ interaction could attenuate EGFR phosphorylation. Computational simulation showed that the β-sheets of LTβ may also serve as a interface for the interaction between LTβ and EGFR-ICD. In vitro binding assay showed that the 5$^{th}$, 8$^{th}$, and 9$^{th}$ β-sheets interacted with LTβ. The in vitro kinase assay also showed that the 5$^{th}$ and 9$^{th}$ β-sheets of LTB suppresses EGFR phosphorylation most significantly. In summary, the data showed that using peptides containing β-sheets of LTβ to compete the interaction between LTβ and EGFR reduces EGF-EGFR binding and EGFR phosphorylation, resulting in sensitization of the resistant HNSCC cells to cetuximab treatment.

Materials and Methods

Cell Lines and Plasmids.

The human head and neck cancer cell line FaDu, OECM1, SAS, Ca9-22, and the human embryonic kidney cell line 293T were described (Yang, M. H. et al. *Oncogene* 31, 2401-2411 (2012)). The pHA-EGFR, pHA-EGFR-ECD, pHA-EGFR-ICD were gifts from Professor Mien-Chie Hung (M.D. Anderson Cancer Center, Houston, Tex., USA). The NF-κB reporter pGL4.32 was provided by Dr. Nien-Jung Chen (Institute of Microbiology and Immunology, National Yang-Ming University). The pCDH-Snail, the unacetylatable mutant pCDH-Snail2R, and pHA-CBP have been previously described (Hsu et al., 2010). The pFLAG-LTB was generated by inserting full-length cDNA into the pFLAG-CMV2, pCDH-CMV-MCS-EF1-puro, vector. The pFLAG-EGFR-V924R and pFLAG-EGFR-K721A were generated by V-to-R mutation of V924 and K-to-A mutation of K721 in the wild-type EGFR construct pHA-EGFR according to a reference study (Red B. et al. *Proc. Natl. Acad. Sci. USA* 110, E3595-604 (2013)). The pLKO.1-shLuc, LTB shRNA, SNAI1 shRNA were obtained from the National RNAi Core Facility of Taiwan for gene silencing. The proximal promoter regions of LTB were cloned into pGL4.2 to generate the promoter reporter constructs pGL4.2-LTB-WT. Site-directed mutagenesis was used for mutating E-boxes of the LTB promoter to generate the mutant reporter construct pGL4.2-LTB-MUT.

RNA-Sequencing, cDNA Microarray Analysis, and Direct Sequencing for Detecting Mutations in Driver Genes.

To examine the mRNA profiles of the Snail-overexpressing FaDu cells (FaDu-Snail) versus the control cells (FaDu-vec), total RNA was collected and sequenced using the Illumina Genome Analyzer II (Illumina, Inc., San Diego, Calif.). The quality of the reads, including the read length and the nucleotide distribution, obtained from the sequencing results was examined. For data analysis, the quality Fastq sequences, which lacked a poly-A tail, ambiguous nucleotides and a 5' adapter but contained the flanking 6-18 nt of a 3' adapter sequence, were trimmed of their adapter sequences, and the identical sequences were then collapsed to unique sequences. The resulting unique sequences that did align with sequences in the mRNA database (UCSC genome browsers) were subjected to further quantification. The sequencing reads were calculated to obtain a reads per kilobase of exon model per million mapped reads (RPKM) value. For examining the gene expression profile of OECM1-Ctx$^R$ and parental OECM1 cells, a microarray by using the Agilent SurePrint G3 Human V2 GE 8X60K Microarray (Agilent Technologies, Inc., Santa Clara, Calif.) were performed. Total RNA collection, cRNA probe preparation, array hybridization, feature selection and computational analysis were performed as previously described. For examining the driver genes mutations in cetuxmab-resistant cells and patient samples, the genomic DNA of the submitted specimen was prepared for library construction. Each library was hybridized to exons and introns from the interested driver genes. For DNA sequencing, libraries were sequenced with 200-cycles pair-end multiplex sequencing on Illumina HiSeq2500 platforms (Illumina, San Diego, Calif., USA). Sequencing reads of 200 bases were trimmed and aligned to a human reference genome (hg19, NCBI build). Variants are reported according to Human Genome Variation Society (HGVS) nomenclature. Categorization of variants was dependent upon literature review, variant existence in a variety of publically available databases, including the Single Nucleotide Polymorphism Database (dbSNP), the Catalogue of Somatic Mutations in Cancer (COSMIC), the 1,000 genome project, and PharmGKB etc.

Gene Set Enrichment Analysis (GSEA).

GSEA was used to assess the degree of association between HNSCC cetuximab resistance (GSE21483) and different gene expression signatures. GSEA was performed using the JAVA program (http://www.broadinstitute.org/gsea). The Snail-regulated signature was defined as the genes upregulated >2 fold in FaDu-Snail compared with the FaDu control cells. The Twist1-regulated SDCSC signature was from the upregulated genes (2 fold) in FaDu-Twist1 cells (GSE19406). The genes that exhibited differences in expression were ranked using a signal-to-noise metric. A q value of <0.05 was considered significant, and the normalized enrichment score (NES) is reported.

Patient Samples.

Three sets of HNSCC samples from the Department of Otolaryngology of Taipei Veterans General Hospital were used in this study. The first set of samples was applied for analyzing the expression of LTB, which contains the samples from 12 HNSCC patients receiving cetuximab treatment and developed recurrent tumors after treatment. The second set of samples was used to analyze the association between the expression of LTB and SNAP, which was obtained from 58 HNSCC patients before treatment. The third set of samples was used for direct sequencing of the driver genes mutation, which contains two patients developed recurrent tumor after cetuximab treatment. In addition, a tumor developed from cetuximab-treatment patients was harvested for primary culture.

Luciferase Reporter Assays.

The reporter constructs (PGL4.2-LTB-WT/PGL4.2-LTB-MUT/pGL4.23 promoter) were co-transfected into HEK-293T, FaDu or OECM1/OECM1-Ctx$^R$ cells with different expression/control vector(s) as indicated in each experiment. A plasmid expressing the bacterial β-galactosidase gene (pCMV-βgal) was co-transfected in each experiment as an internal control for transfection efficiency. Cells were harvested after 48 hours of transfection and luciferase activities were assayed. The relative promoter activities were expressed as the fold-change in luciferase activity after normalization to β-galactosidase activity.

Chip Assay.

The cells were cross-linked with 1% foimaldehyde and harvested with SDS buffer (50 mM Tris [pH 8.0], 0.5% SDS, 100 mM NaCl, 5 mM EDTA, and protease inhibitors). After centrifugation, the nuclear fractions were resuspended and subjected to sonication, and then the lysates were incubated with protein A+G beads conjugated to specific antibodies for different proteins or an IgG control. Then, the DNA-protein complexes were eluted by incubation at 37° C. with 50:1 of 10 mM dithiothreitol (DTT) for 30 min. The regions of interest were amplified from precipitated samples by real-time PCR. Each sample was assayed in triplicate, and the amount of precipitated DNA was calculated as the percentage of input sample.

Electrophoretic Mobility Shift Assay.

The DNA binding amount of NF-κB was determined using the NF-κB EMSA kit (No. GS0030, Signosis, Inc., Santa Clara, Calif.). Briefly, a biotin-labelled DNA probe containing specific binding sequence of NF-κB was incubated with the nuclear extracts from OECM1/OECM1-Ctx$^R$ cells. Electrophoresis was performed and the gel was transferred to a nylon membrane. NF-κB binding to the probe was detected by strepatvidin-HRP and a chemiluminescent substrate. In the competition assay, excess amounts of unlabelled competitors were added prior to the labelled probes. The concentration of the probe was 20 ng/μl.

Cell Viability Assay and Determination of Combination Index (CI).

A total of $5\times10^4$ cells per well were seeded in a 96-well plate with triplicate and incubated for 24 h and then treated with different concentrations of indicated drugs. After 24 h treatment, the medium was removed. The MTT assay solution was added to each well, and the plate was incubated for 1 h at 37° C. After incubation, the solution was carefully discarded and dimethyl sulphoxide was added to dissolve newly formed mitochondrial MTT crystals. Finally, the plate was read using a microplate reader at 540 nm. Based on the data of cell viability assay, $IC_{50}$-value calculation was performed by Sigmaplot 10.0 (Systat Software Inc., San Jose, Calif.).

Xenotransplantation into Zebrafish Embryos.

CFSE (5(6)-Carboxyfluorescein N-hydroxysuccinimidyl ester) was used to label the cells because it is stable and dilutes stoichiometrically as cells divide. The cells were incubated in CellTrace™ CFSE (1 Degree Bio Inc., Toronto, Canada)/PBS working solution (25 μM) for 15 minutes at 37° C. then were centrifuged and washed. The cells were diluted in PBS to 2.3 nl which contains 100 tumor cells. A glass transplantation needle was used to transfer the CFSE-labeled cells into the perivitelline cavity of the two-day-old zebrafish embryo. After transplantation, embryos were checked for presence of labeled cells three hours later, make sure no leaking cells. The embryo then placed in a 96 well plate, 200 μl per well containing one zebrafish embryo, and placed in the incubator which automatically raise 1° C. every six hours, and reached 37° C. in two days. One day post-injection, the drugs were added into each well. Twenty embryos in 20 wells for each testing drug and control were used. The tumor cells were observed under a microscope for the proliferation behavior in the zebrafish embryo, and images were taken individually for one-day-post injection (ldpi) and three day-post injection (3 dpi). Following image acquisition, embryos were fixed overnight with paraformaldehyde (4%) at RT, and perform immunostaining with primary antibody against Ki67 (1:200, Arigo Biolaboratories Corp., Hsinchu, Taiwan) to verify the proliferation.

Clonogenecity Assay 5,000 cells/well were seeded into 24-well plates. After 10 days of culturing, cells were washed by cold PBS twice and fixed by 4% paraformaldehyde for 1 hour. Cells then were stained by 0.005% crystal violet at 4° C. overnight. Colonies with a diameter larger than 0.5 mm were counted.

Saturation Binding Assay.

ELISA 96-well plates were captured with 3 μg/ml anti-EGFR antibody (Abeam) in 0.2 M sodium phosphate buffer (pH 6.5) at 100 μl/well overnight at room temperature. The plates were then rinsed 3 times with PBS with 0.05% Tween-20 (PBST) and blocked with 200 μl/well of 1% BSA solution at 37° C. for 2 hours. After rinsing 3 times with PBST, 100 μl/well of OECM1-RIPA lysates or RIPA buffer only as a negative control were added and incubated at 37° C. for 1.5 hours. The plates were then washed with 400 μl/well of PBST 3 times, followed by addition of recombinant human biotin-EGF at a series of diluted concentrations in RIPA buffer. After incubation at 37° C. for 1.5 hours, wells were washed with 400 μl/well of PBST 3 times, added by 100 μl/well of streptavidin-conjugated HRP (1:2,000 in blocking buffer), and incubated for 30 minutes at room temperature. The wells were washed again with PBST 3 times, and 100 μl/well of TMB as a peroxidase substrate were added and incubated for 30 minutes at room temperature. The reaction was terminated by addition of 50 μl/well of stop solution. The optical density was determined at 450 nm, corrected by subtraction of readings at 570 nm, using a BioTek Synergy Neo multi-mode reader. The Kd was estimated by the above binding data and then transformed to create a Scatchard plot with GraphPad Prism program (version 6; Prism Software Inc.).

Flow Cytometry.

To analyze EGF binding, the cells were resuspended, incubated in a PE-conjugated anti-EGF antibody and evaluated using a Cytomics FC 500 instrument (Beckman-Coulter Inc., Fullerton, Calif.). The EGF-bound populations were defined compared with the IgG control group.

Quantitative RT-PCR.

Quantitative PCR was performed using the StepOne-Plus real-time PCR system (Applied Biosystems Inc., Foster City, Calif.).

Immunoprecipitation and Immunoblotting.

For immunoprecipitation, the lysates were mixed with an equal amount of Co-IP buffer. The primary antibody or IgG was added to the lysates, and the reactions were incubated and then blocked with protein A beads overnight. The beads were collected and washed gently prior to immunoblotting. ImageJ software was used for densitometric measurements of the western blots.

Immunofluorescence.

The cells were seeded on poly-L-lysine-coated slides, fixed with 4% paraformaldehyde, permeabilized with 0.5% Triton X-100, and blocked with 1% BSA. Hoechst 33342 was used for nuclear staining. The images were captured using an Olympus FluoView FV10i laser scanning confocal microscope (Olympus Corporation, Tokyo, Japan) equipped with a 60x oil objective (Olympus UPLSAPO 60XO, NA 1.35). Images were collected sequentially using the confocal laser scanning microscope and analyzed using Olympus FV10-ASW Version 3.0 Software.

Reagents.

Cetuximab (Erbitux™) was from Merck (Merck KGaA, Darmstadt, Germany), afatinib (GIOTRIF®) was from Boehringer Ingelheim GmbH (Ingelheim, Germany), bortezomib (VELCADE®) was from Millennium Pharmaceuticals, Inc. (Cambridge, Mass.). Pathenoloide, LY294002, rapamycin, and S31-201 were from Sigma (Sigma-Aldrich Corp., St. Louis, Mo.). The antibodies for recognizing lysine 146- or lysine 187-acetylated Snail were described in previous study.

Statistics.

The independent t-test was performed to compare the continuous variation of two groups, and was also applied to analyse the ONCOMINE dataset. $\chi2$ test or Fisher's exact test was applied for comparison of dichotomous variables. The Pearson correlation test was used for analysing the correlation between two continuous factors. The log-rank t-test was used for survival analysis. P-values<0.05 were considered to be significant. For animal studies, no statistical method was used to predetermine the sample size. The experiments were not randomised. The investigators were not blinded to allocation during experiments and outcome assessment.

Although various exemplary embodiments have been described in detail with particular reference to certain exemplary aspects thereof, it should be understood that the subject matter disclosed herein is capable of other different embodiments, and its details are capable of modifications in various obvious respects. As is readily apparent to those skilled in the art, variations and modifications can be affected while remaining within the spirit and scope of the disclosure. Accordingly, the foregoing disclosure, description, and figures are for illustrative purposes only, and do not in any way limit the invention, which is defined only by the claims.

What is claimed is:

1. A method of reducing or overcoming acquired resistance to cetuximab in a patient, the method comprising administering to the patient a composition comprising a peptide that comprises an amino acid sequence of QDGLYYLYCLVGYR (SEQ ID NO: 5) or ERVYVNISH (SEQ ID NO: 9) or a combination thereof.

2. The method of claim 1, wherein the patient has an elevated expression level of lymphotoxin-β (LTβ).

3. The method of claim 1, wherein the peptide comprises an amino acid sequence of ERVYVNISH (SEQ ID NO: 9) or QDGLYYLYCLVGYR (SEQ ID NO: 5).

4. The method of claim 1, wherein the patient has a tumor that has acquired resistance to cetuximab.

5. The method of claim 4, wherein the patient is characterized by the absence of phosphatidylinositol-4,5-bisphosphate 3-kinase catalytic subunit alpha (PIK3CA), KRAS proto-oncogene (KRAS), HRAS proto-oncogene (HRAS), NRAS proto-oncogene (NRAS), and/or epidermal growth factor receptor (EGFR) gene mutation.

6. The method of claim 4, wherein erb-b2 receptor tyrosine kinase 2 (ERBB2) gene is not amplified in the tumor cells.

7. The method of claim 1, further comprising anti-EGFR antibody for treating cancer, wherein the cancer is selected from the group consisting of head and neck cancer, head and neck squamous cell carcinoma (HNSCC) and colorectal cancer.

8. The method of claim 7, wherein the anti-EGFR antibody is cetuximab.

9. The method of claim 7, wherein the cancer is head and neck squamous cell carcinoma (HNSCC).

10. A pharmaceutical composition comprising a combination of anti-EGFR antibody and a peptide, and wherein the peptide comprises an amino acid sequence of QDGLYYLYCLVGYR (SEQ ID NO: 5) or ERVYVNISH (SEQ ID NO: 9) or a combination thereof, and a pharmaceutically effective carrier.

11. The pharmaceutical composition of claim 10, wherein the peptide comprises an amino acid sequence of QDGLYYLYCLVGYR (SEQ ID NO: 5).

12. The pharmaceutical composition of claim 10, wherein the peptide comprises an amino acid sequence of ERVYVNISH (SEQ ID NO: 9).

13. The pharmaceutical composition of claim 10, wherein the anti-EGFR antibody is cetuximab.

14. A method of treating cancer wherein the cancer is resistant to cetuximab, the method comprising administering an effective amount of a pharmaceutical composition to a patient suffering therefrom, wherein the cancer is selected from the group consisting of head and neck cancer, head and neck squamous cell carcinoma (HNSCC) and colorectal cancer.

15. The method of claim 14, wherein the patient has an elevated expression level of lymphotoxin-β (LTβ).

16. The method of claim 14, wherein the patient has a tumor that has acquired resistance to cetuximab.

17. The method of claim 16, wherein the patient is characterized by the absence of phosphatidylinositol-4,5-bisphosphate 3-kinase catalytic subunit alpha (PIK3CA), KRAS proto-oncogene (KRAS), HRAS proto-oncogene (HRAS), NRAS proto-oncogene (NRAS), and/or epidermal growth factor receptor (EGFR) gene mutation.

18. The method of claim 16, wherein erb-b2 receptor tyrosine kinase 2 (ERBB2) gene is not amplified in the tumor cells.

* * * * *

SEQUENCE LISTING

<160> NUMBER OF SEQ ID NOS: 11

<210> SEQ ID NO 1
<211> LENGTH: 244
<212> TYPE: PRT
<213> ORGANISM: Homo sapiens

<400> SEQUENCE: 1

```
Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

<210> SEQ ID NO 2
<211> LENGTH: 13
<212> TYPE: PRT
<213> ORGANISM: Artificial Sequence
<220> FEATURE:
<223> OTHER INFORMATION: beta-sheet of LTbeta

<400> SEQUENCE: 2

```
Leu Pro Ala Ala His Leu Ile Gly Ala Pro Leu Lys Gly
1               5                   10
```

<210> SEQ ID NO 3
<211> LENGTH: 15
<212> TYPE: PRT
<213> ORGANISM: Artificial Sequence
<220> FEATURE:
<223> OTHER INFORMATION: beta-sheet of LTbeta

```
<400> SEQUENCE: 3

Gln Gly Leu Gly Trp Glu Thr Thr Lys Glu Gln Ala Phe Leu Thr
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: beta-sheet of LTbeta

<400> SEQUENCE: 4

Gly Thr Gln Phe Ser Asp Ala Glu Gly Leu Ala Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: beta-sheet of LTbeta

<400> SEQUENCE: 5

Gln Asp Gly Leu Tyr Tyr Leu Tyr Cys Leu Val Gly Tyr Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: beta-sheet of LTbeta

<400> SEQUENCE: 6

Gln Gly Arg Ser Val Thr Leu Arg Ser Ser Leu Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: beta-sheet of LTbeta

<400> SEQUENCE: 7

Thr Pro Glu Leu Leu Leu Glu Gly Ala Glu Thr Val Thr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: beta-sheet of LTbeta

<400> SEQUENCE: 8

Trp Tyr Thr Ser Val Gly Phe Gly Gly Leu Val Gln Leu Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: beta-sheet of LTbeta
```

```
<400> SEQUENCE: 9

Glu Arg Val Tyr Val Asn Ile Ser His
1               5

<210> SEQ ID NO 10
<211> LENGTH: 10
<212> TYPE: PRT
<213> ORGANISM: Artificial Sequence
<220> FEATURE:
<223> OTHER INFORMATION: beta-sheet of LTbeta

<400> SEQUENCE: 10

Lys Thr Phe Phe Gly Ala Val Met Val Gly
1               5                   10

<210> SEQ ID NO 11
<211> LENGTH: 58
<212> TYPE: DNA
<213> ORGANISM: Artificial Sequence
<220> FEATURE:
<223> OTHER INFORMATION: shRNA

<400> SEQUENCE: 11
ccggcgagag ggtgtacgtc aacatctcga gatgttgacg tacaccctct cgtttttg      58
```